(12) United States Patent
Tearney et al.

(10) Patent No.: US 11,633,104 B2
(45) Date of Patent: *Apr. 25, 2023

(54) OPTICAL FIBER, LIGHT TUNNEL, AND LENS WHICH PROVIDE EXTENDED FOCAL DEPTH OF AT LEAST ONE ANATOMICAL STRUCTURE AT A PARTICULAR RESOLUTION

(71) Applicant: The General Hospital Corporation, Boston, MA (US)

(72) Inventors: Guillermo J. Tearney, Cambridge, MA (US); Brett Eugene Bouma, Quincy, MA (US); Joseph A. Gardecki, Acton, MA (US); Linbo Liu, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 25 days.

This patent is subject to a terminal disclaimer.

(21) Appl. No.: 16/577,435

(22) Filed: Sep. 20, 2019

(65) Prior Publication Data
US 2020/0046227 A1 Feb. 13, 2020

Related U.S. Application Data

(63) Continuation of application No. 15/588,404, filed on May 5, 2017, now Pat. No. 10,463,254, which is a
(Continued)

(51) Int. Cl.
*A61B 5/00* (2006.01)
*G02B 6/32* (2006.01)
*G01B 9/02091* (2022.01)

(52) U.S. Cl.
CPC .......... *A61B 5/0066* (2013.01); *A61B 5/0044* (2013.01); *A61B 5/0075* (2013.01);
(Continued)

(58) Field of Classification Search
CPC ... A61B 5/0066; A61B 5/0075; A61B 5/0044; A61B 5/0084; G01B 9/02091; G02B 6/32
See application file for complete search history.

(56) References Cited

U.S. PATENT DOCUMENTS 4,576,435 A * 3/1986 Nishioka ............. G02B 6/4298
607/93
4,744,615 A * 5/1988 Fan ..................... G03F 7/70583
219/121.61
(Continued)

FOREIGN PATENT DOCUMENTS

DE 294805 A5 * 10/1991

OTHER PUBLICATIONS

Nikon, "Perfect Lens Characteristics" Microscopy U The Source for Microscopy Education, https://www.microscopyu.com/tutorials/perfectlens#:~:text=A%20parallel%2C%20paraxial%20beam%20of,labeled%20Focus%20in%20Figure%201) (printed Jun. 16, 2022) (Year: 2022).*

*Primary Examiner* — Hwa Andrew Lee
(74) *Attorney, Agent, or Firm* — Quarles & Brady LLP

(57) ABSTRACT

Exemplary embodiments of systems and methods can be provided which can generate data associated with at least one portion of a sample. For example, at least one first radiation can be forwarded to the portion through at least one optical arrangement. At least one second radiation can be received from the portion which is based on the first radiation. Based on an interaction between the optical arrangement and the first radiation and/or the second radiation, the optical arrangement can have a first transfer function. Further, it is possible to forward at least one third radiation to the portion through such optical arrangement (or through another optical arrangement), and receive at least one fourth radiation from the portion which is based on the third radiation. Based on an interaction between the optical
(Continued)

arrangement (or the other optical arrangement) and the third radiation and/or the fourth radiation, the optical arrangement (or the other optical arrangement) can have a second transfer function. The first transfer function can be at least partially different from the second transfer function. The data can be generated based on the second and fourth radiations.

22 Claims, 26 Drawing Sheets

Related U.S. Application Data continuation of application No. 14/455,355, filed on Aug. 8, 2014, now Pat. No. 9,642,531, which is a continuation of application No. 13/042,230, filed on Mar. 7, 2011, now Pat. No. 8,804,126.

(60) Provisional application No. 61/311,272, filed on Mar. 5, 2010, provisional application No. 61/311,171, filed on Mar. 5, 2010.

(52) U.S. Cl.
CPC ........ *A61B 5/0084* (2013.01); *G01B 9/02091* (2013.01); *G02B 6/32* (2013.01)

(56) References Cited

U.S. PATENT DOCUMENTS

| | | | | |
|---|---|---|---|---|
| 8,804,126 | B2* | 8/2014 | Tearney | A61B 5/0044 |
| | | | | 356/479 |
| 8,896,838 | B2* | 11/2014 | Tearney | G02B 6/32 |
| | | | | 356/450 |
| 9,081,148 | B2* | 7/2015 | Tearney | G01B 9/02091 |
| 9,408,539 | B2* | 8/2016 | Tearney | A61B 5/0044 |
| 2005/0063604 | A1* | 3/2005 | Kita | G06T 5/008 |
| | | | | 382/254 |
| 2006/0093276 | A1* | 5/2006 | Bouma | G02B 6/32 |
| | | | | 385/72 |
| 2006/0158655 | A1 | 7/2006 | Everett et al. | |
| 2006/0187520 | A1* | 8/2006 | Bierhuizen | G02F 1/13362 |
| | | | | 359/247 |
| 2007/0171430 | A1* | 7/2007 | Tearney | G02B 27/46 |
| | | | | 356/512 |
| 2018/0259317 | A1* | 9/2018 | Tearney | G01B 9/02035 |

* cited by examiner

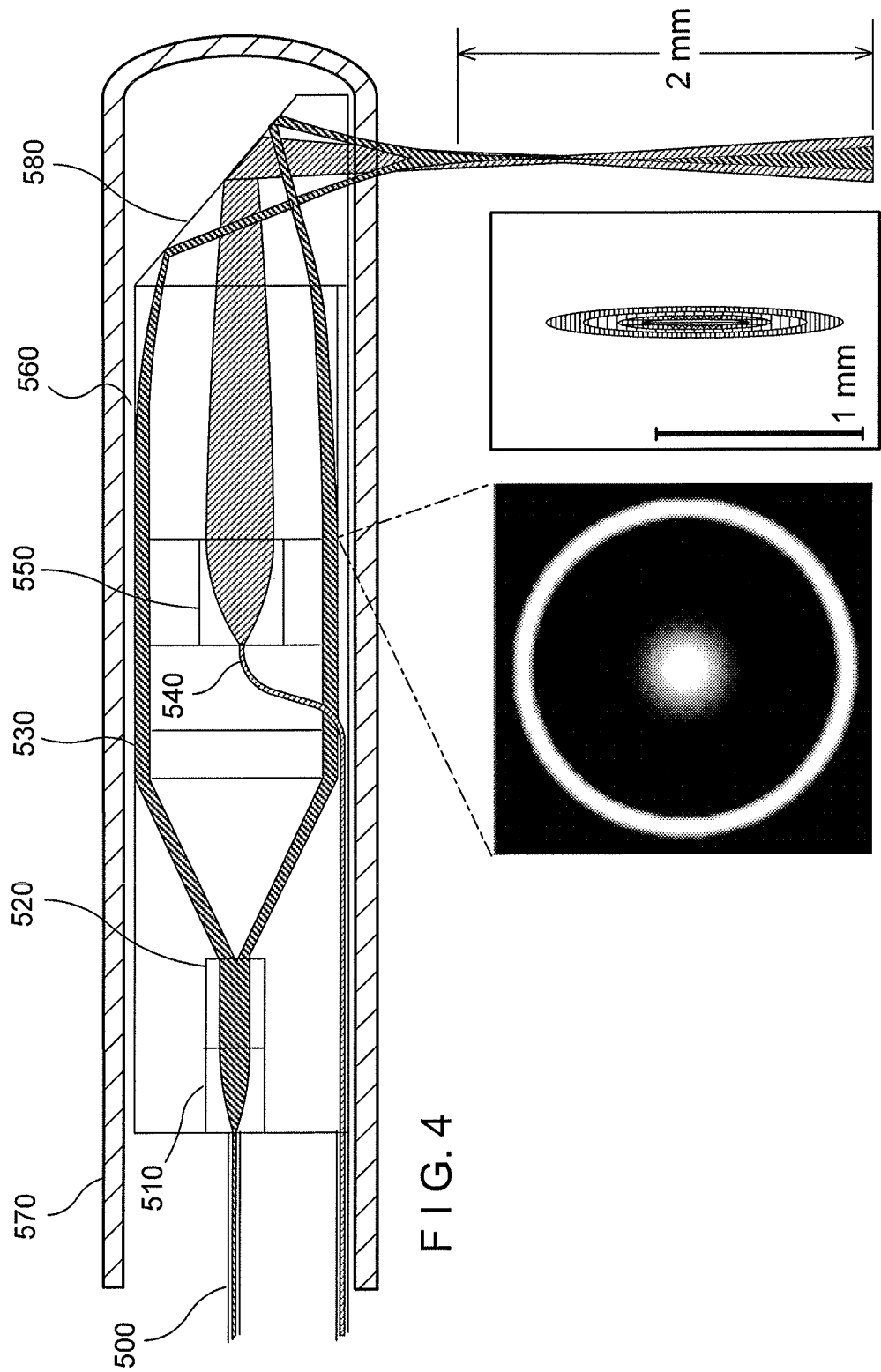

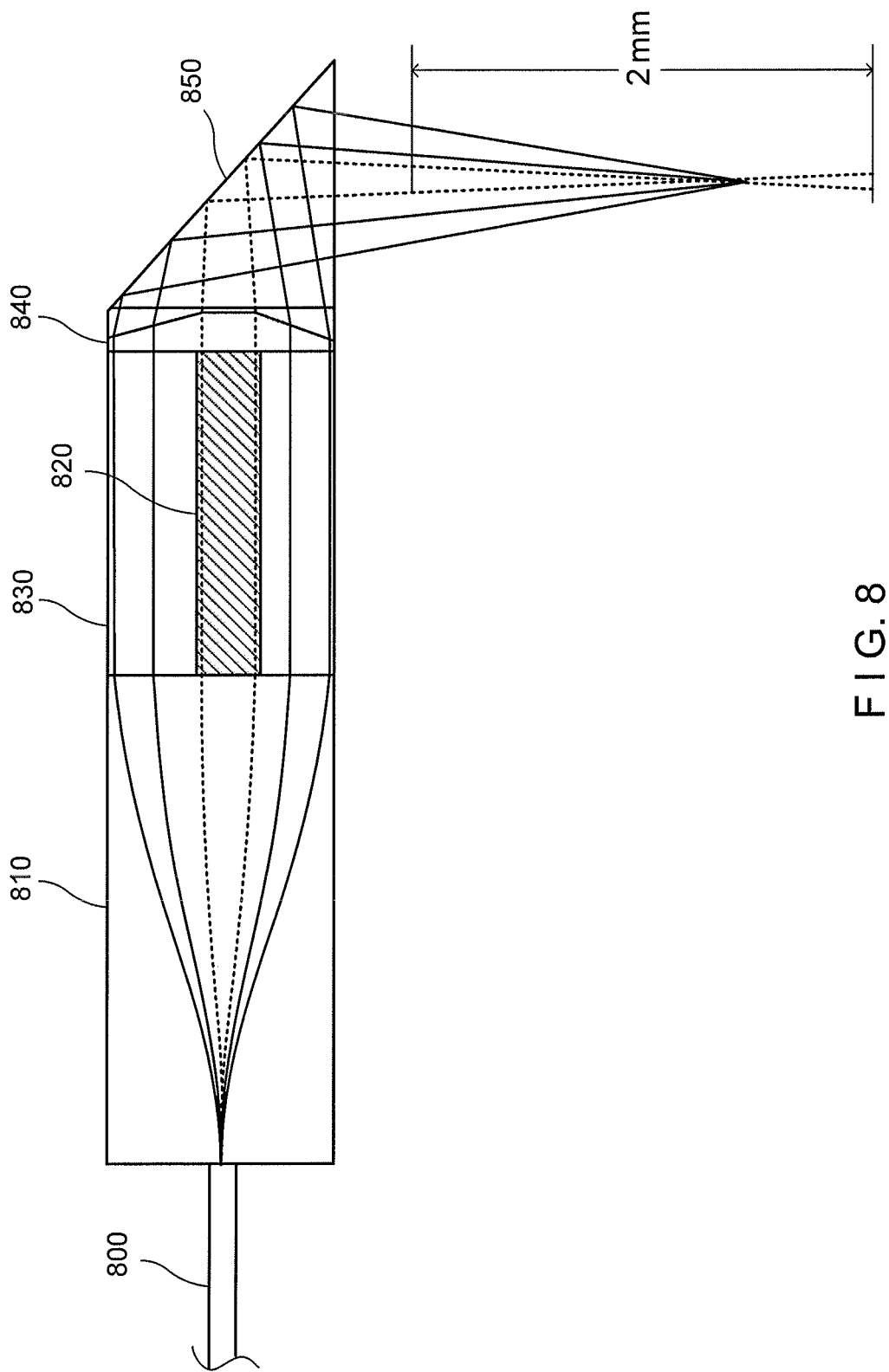
F I G. 8

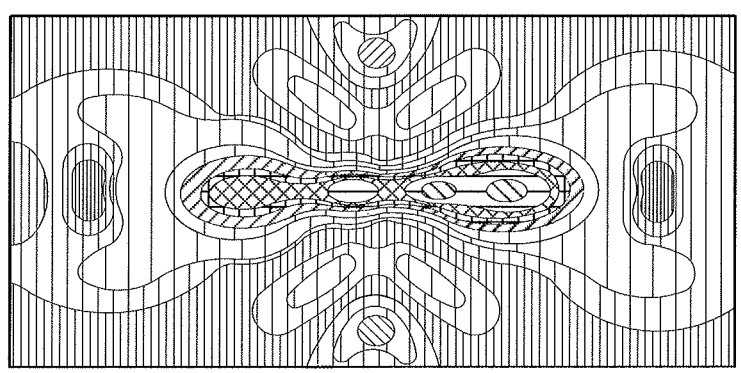
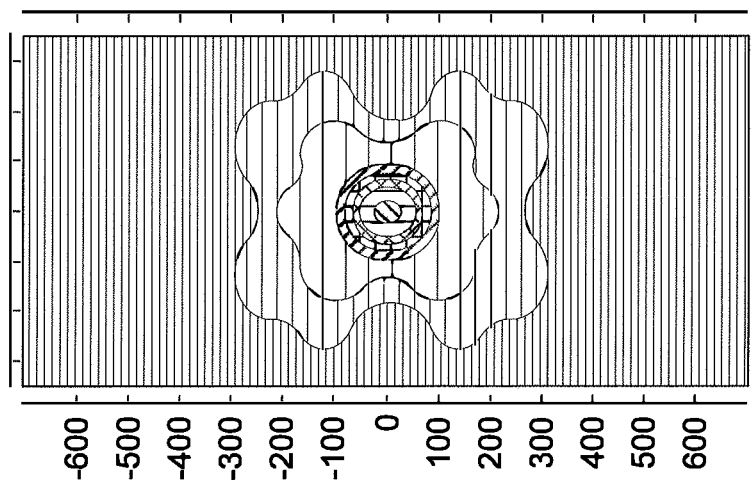

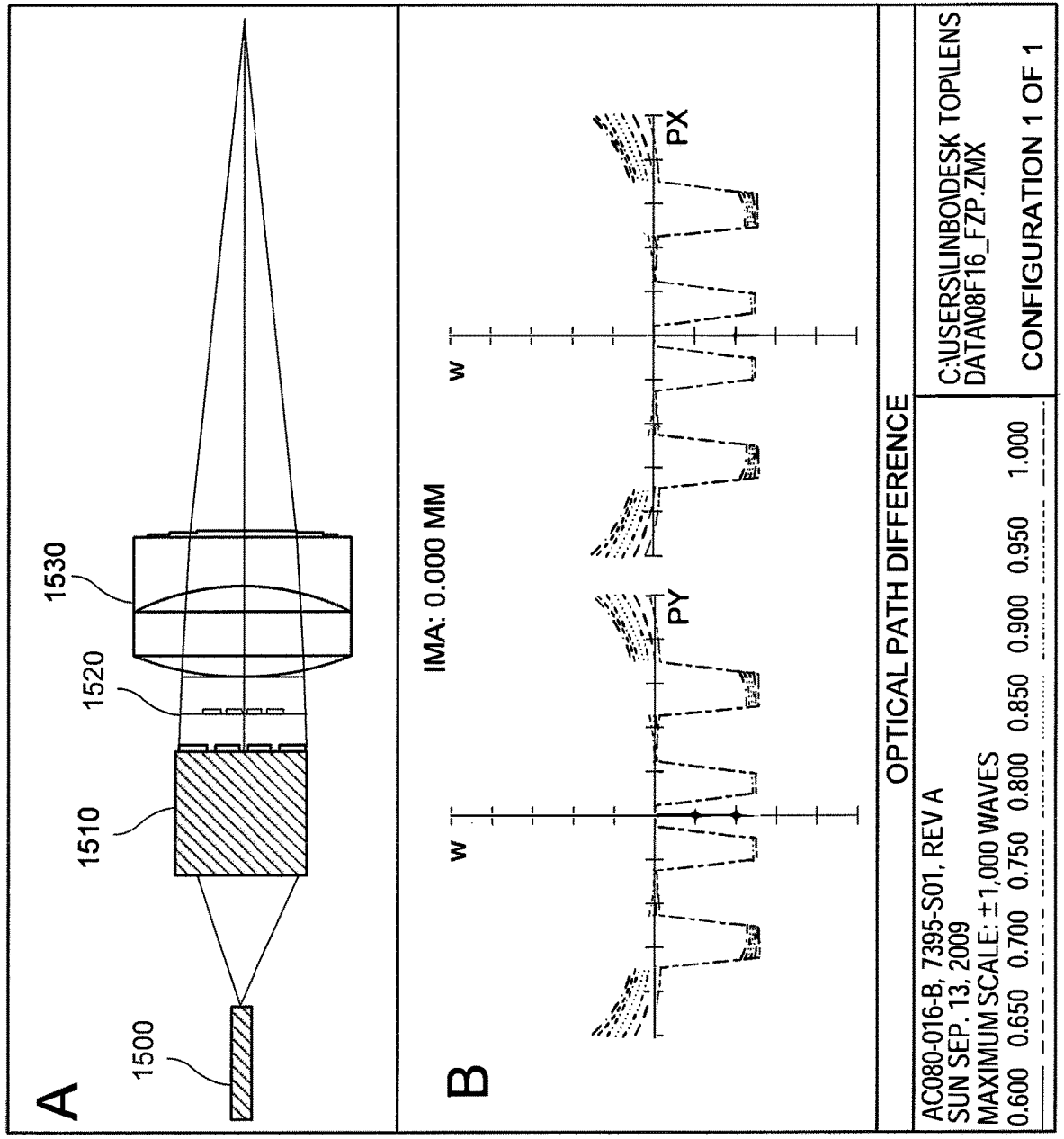

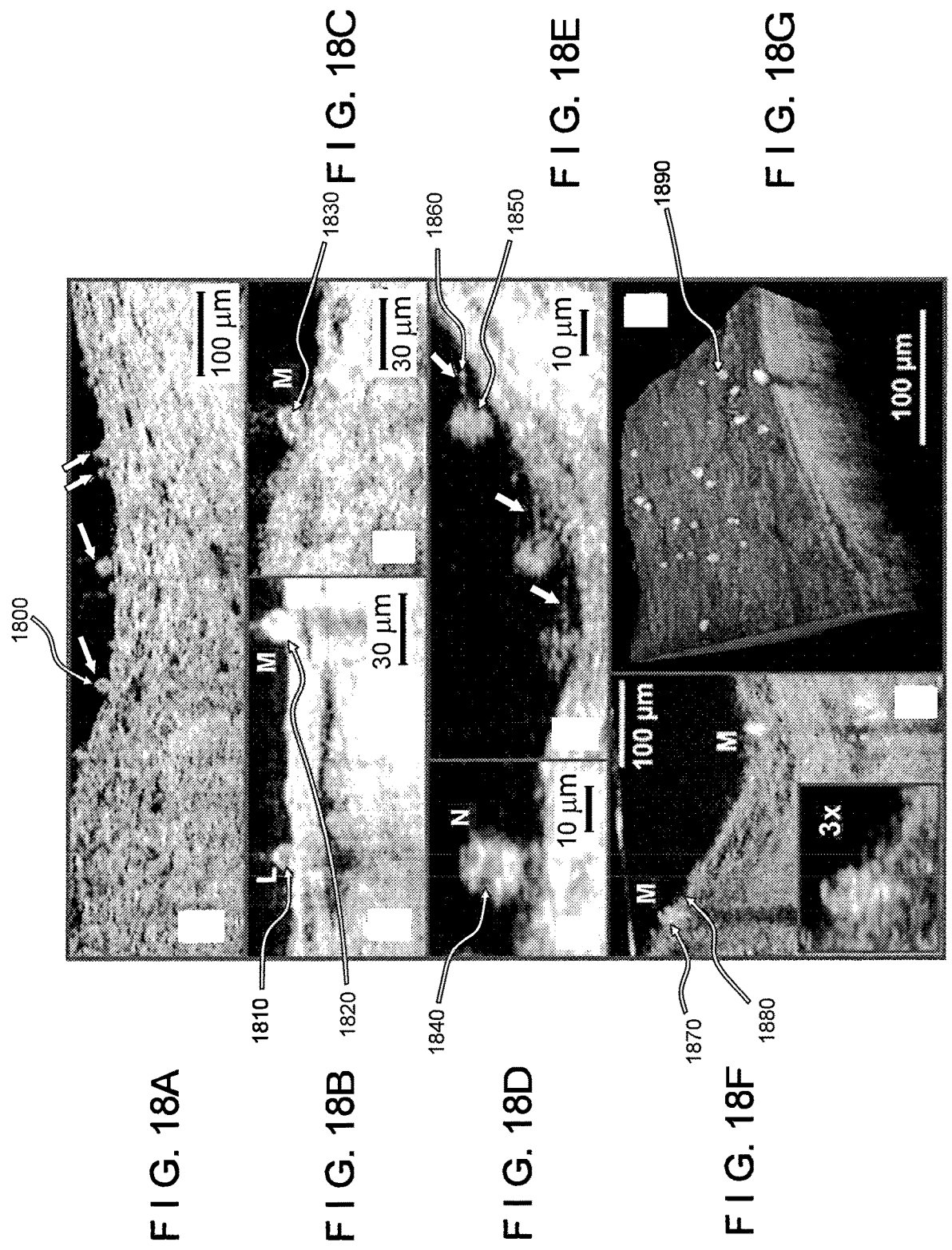

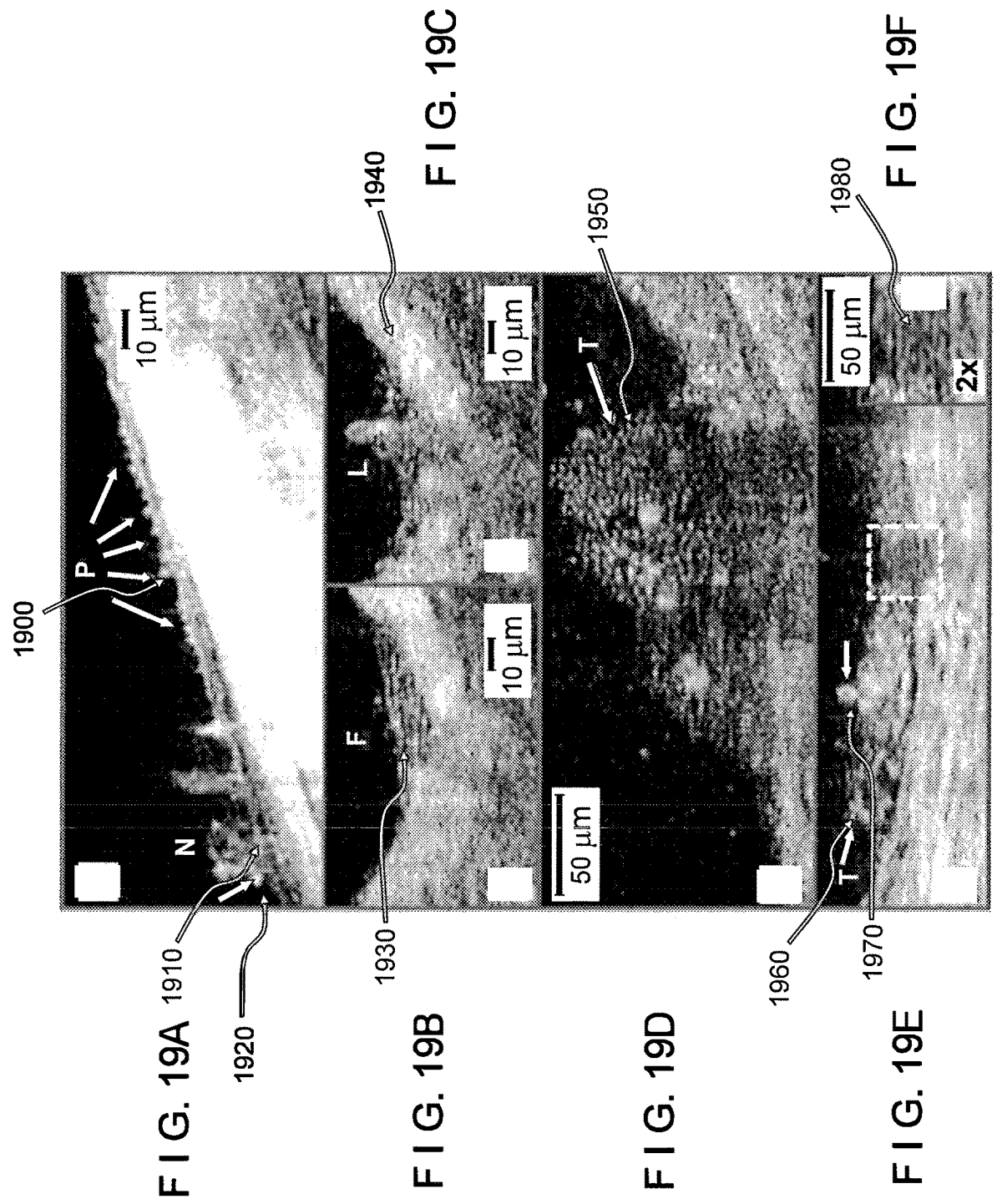

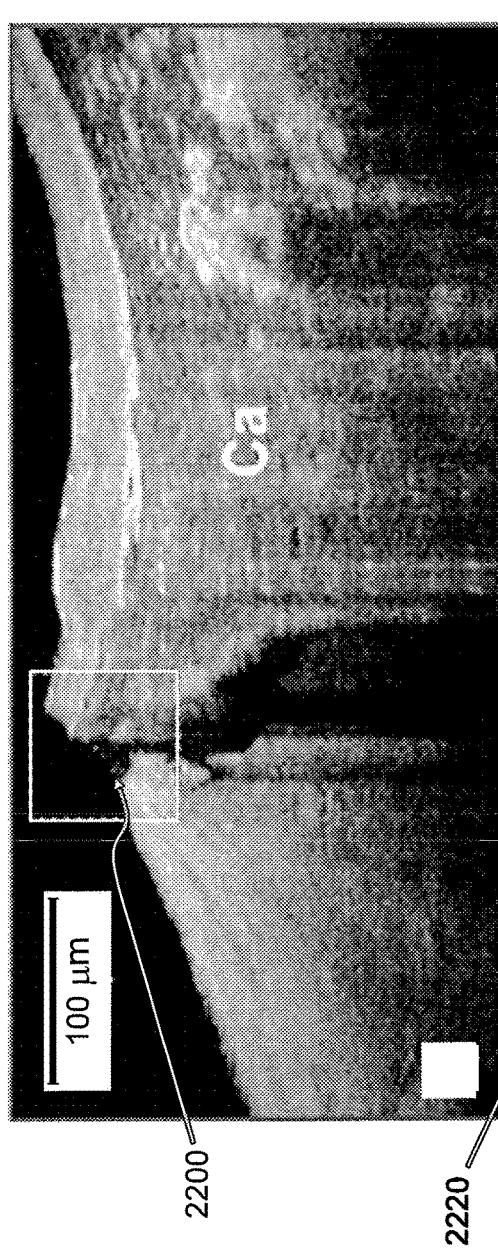
FIG. 22A
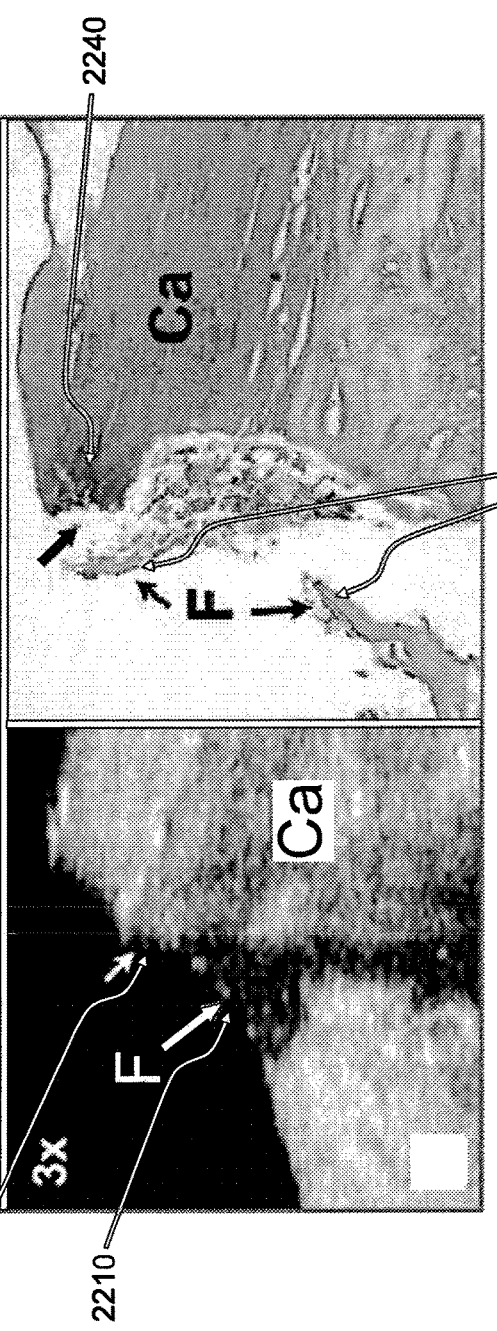
FIG. 22B
FIG. 22C

| 2760 | | 2770 | | 2780 |
|---|---|---|---|---|
| Forward at least one first radiation to at least one portion of a sample through at least one first optical arrangement, and receive at least one second radiation from the portion which is based on the first radiation, where, based on an interaction between the first optical arrangement and the first radiation and/or the second radiation, the first optical arrangement has a first transfer function | 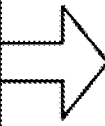 | Forward at least one third radiation to the portion through at least one second optical arrangement, and receive at least one fourth radiation from the portion which is based on the third radiation, where, based on an interaction between the second optical arrangement and the third radiation and/or the fourth radiation the second optical arrangement has a second transfer function, and where the first transfer function is at least partially different from the second transfer function | 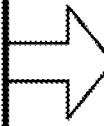 | Generate data associated with the portion of the sample based on the second and fourth radiations |

FIG. 27B

OPTICAL FIBER, LIGHT TUNNEL, AND LENS WHICH PROVIDE EXTENDED FOCAL DEPTH OF AT LEAST ONE ANATOMICAL STRUCTURE AT A PARTICULAR RESOLUTION

CROSS-REFERENCE TO RELATED APPLICATION(S)

This application is a continuation of U.S. patent application Ser. No. 15/588,404 which is a continuation of U.S. patent application Ser. No. 14/455,355 filed Aug. 8, 2014, which issued as U.S. Pat. No. 9,642,531 on May 9, 2017, which is a continuation of U.S. patent application Ser. No. 13/042,230 filed Mar. 7, 2011, which issued as U.S. Pat. No. 8,804,126 on Aug. 12, 2014, and which is based upon and claims the benefit of priority from U.S. Provisional Patent Application Ser. Nos. 61/311,171 and 61/311,272, both filed Mar. 5, 2010, the entire disclosures of which are incorporated herein by reference.

FIELD OF THE DISCLOSURE

The present disclosure relates to exemplary embodiments of imaging systems, apparatus and methods, and more specifically to methods, systems and computer-accessible medium which provide microscopic images of at least one anatomical structure at a particular resolution.

BACKGROUND INFORMATION

Coronary artery disease (CAD) and its clinical manifestations, including heart attack or acute myocardial infarction (AMI), is the number one cause of mortality in the US, claiming nearly 500,000 lives and costing approximately $400B per year. Topics relevant to the pathophysiology of CAD, such as the development and progression of coronary atherosclerotic lesions, plaque rupture and coronary thrombosis, and the arterial response to coronary device and pharmacologic therapies are therefore of great significance today. These biological processes can be mediated by molecular and cellular events that occur on a microscopic scale. Certain progress in understanding, diagnosing, and treating CAD has been hindered by the fact that it has been difficult or impossible to interrogate the human coronary wall at cellular-level resolution in vivo.

Over the past decade, intracoronary optical coherence tomography (OCT) has been developed, which is a catheter-based technique that obtains cross-sectional images of reflected light from the coronary wall. Intracoronary OCT has a spatial resolution of 10 µm, which is an order of magnitude better than that of the preceding coronary imaging method, intravascular ultrasound (IVUS). In the parent R01, a second-generation form of OCT has been developed, i.e., termed optical frequency domain imaging (OFDI), that has very high image acquisition rates, making it possible to conduct high-resolution, three-dimensional imaging of the coronary vessels. In addition, a flushing method has been developed which, in combination with the high frame rate of OFDI, can overcome at least some of the obstacles of blood interference with the OCT signal. As a direct result, it may be preferable to perform intracoronary OCT procedures in the clinical setting. Indeed, certain interventional cardiology applications for OCT have emerged, and growing the field exponentially. It is believed that OCT can become a significant imaging modality for guiding coronary interventions worldwide.

Since the technology developed in the parent R01 has been translated and facilitated for a clinical practice through the distribution of commercial OFDI imaging systems, it may be preferable to review macromolecules and cells involved in the pathogenesis of CAD.

For example, a transverse resolution in OCT procedure(s) can be determined by the catheter's focal spot size. To improve the resolution, it is possible to increase the numerical aperture of the lens that focuses light into the sample. This conventional method, however, neglects the intrinsic compromise between transverse resolution and depth of field in cross-sectional OCT images and results in images in which only a narrow depth range is resolved.

An alternative approach can exploit the unique characteristics of Bessel, or "non-diffracting" beams to produce high transverse resolution over enhanced depths-of-field. Bessel beam illumination and detection of light reflected from the sample, however, can suffer from a significant reduction in contrast and detection efficiency. Thus, there may be a need to overcome at least some of the deficiencies associated with the conventional arrangements and methods described above.

As briefly indicated herein above, certain exemplary embodiments of the present disclosure can be associated and/or utilize analysis and manipulation of a coherent transfer function (CTF) of an exemplary OCT system. The current invention is instead based on an analysis and manipulation of the coherent transfer function (CTF) of an OCT system. The CTF can be considered a coherent extension of a modulation transfer function (MTF) and an optical transfer function (OTF). Thus, for example, for non-interferometric systems, the MTF or OTF can be manipulated and utilized according to certain exemplary embodiments. In general, the quality of an optical system can be assessed by comparing its transfer function to that of a diffraction-limited optical system. FIG. 1 shows a graph of coherent transfer functions (CTFs) for, e.g., a diffraction limited 2.5 µm diameter spot and 2.5 µm spot with an extended focal range of 2.0 mm, produced by Bessel beam illumination and detection. As illustrated in FIG. 1, the transfer function of a Bessel beam illumination and detection 100 can have spatial frequencies that exceed a diffraction-limited system 110, although it likely sacrifices low- and mid-range spatial frequencies, possibly resulting in reduced contrast and detection sensitivity.

Thus, there may be a need to overcome at least some of the deficiencies associated with the conventional arrangements and methods described above.

SUMMARY OF EXEMPLARY EMBODIMENTS OF THE DISCLOSURE

To address and/or overcome such deficiencies, one of the objects of the present disclosure is to provide exemplary embodiments of systems, methods and computer-accessible medium according to the present disclosure, which can provide microscopic images of at least one anatomical structure at a particular resolution. Another object of the present disclosure is to overcome a limited depth of focus limitations of conventional Gaussian beam and spatial frequency loss of Bessel beam systems for OCT procedures and/or systems and other forms of extended focal depth imaging.

According to another exemplary embodiment of the present disclosure, more than two imaging channels can illuminate/detect different Bessel and/or Gaussian beams. In yet a further exemplary embodiment, different transfer functions can be illuminated and/or detected. The exemplary combination of images obtained with such additional exemplary beams can facilitate the μOCT CTF to be provided to the diffraction-limited case, and can also facilitate a depth-of-field extension even further.

Accordingly, exemplary embodiments of systems and methods can be provided which can generate data associated with at least one portion of a sample. For example, at least one first radiation can be forwarded to the portion through at least one optical arrangement. At least one second radiation can be received from the portion which is based on the first radiation. Based on an interaction between the optical arrangement and the first radiation and/or the second radiation, the optical arrangement can have a first transfer function. Further, it is possible to forward at least one third radiation to the portion through such optical arrangement (or through another optical arrangement), and receive at least one fourth radiation from the portion which is based on the third radiation. Based on an interaction between the optical arrangement (or the other optical arrangement) and the third radiation and/or the fourth radiation, the optical arrangement (or the other optical arrangement) can have a second transfer function. The first transfer function can be at least partially different from the second transfer function. The data can be generated based on the second and fourth radiations.

According to another exemplary embodiment of the present disclosure, when the first and third radiations impact the optical arrangement(s) having an optical aperture, the resultant respective radiations are at least partially focused to (i) a depth of focus and/or (ii) a focal range that is greater than approximately a Raleigh range of a full aperture of illumination. A spot diameter of focus can be less than 10 μm, and the depth of the focus or the focal range can be greater than approximately 1 mm. Alternatively, a spot diameter of can be is less than 10 μm, and the depth of the focus or the focal range is greater than approximately 0.5 mm. Further, a spot diameter of focus can be less than 10 μm, and the depth of the focus or the focal range can be greater than approximately 2 mm. In addition, one of the first radiation, the second radiation, the third radiation or the fourth radiation can be at least partially radially offset from another one of the first radiation, the second radiation, the third radiation or the fourth radiation with respect to respect to a center of the optical arrangement(s).

In a further exemplary embodiment of the present disclosure, it is possible to receive at least one fifth radiation from a reference arrangement, combine the second radiation and/or the fourth radiation with at least one fifth radiation to generate a further radiation, and generate the data as a further function of the further radiation. The first radiation and/or the third radiation can be generated by a broad-band source arrangement and/or a wavelength swept source arrangement. The broad-band source arrangement and/or the wavelength swept source arrangement can generate a radiation which can have a total spectral range that is greater than about 50 nm.

According to still another exemplary embodiment of the present disclosure, the optical arrangement(s) can include an axicon arrangement, a masking arrangement, a defractive optical element, an annulus, a diffractive element, a lens, an apodized lens and/or a diffractive element. Further, the optical arrangement can include at least two optical arrangements, and the first transfer function can be associated with one of the optical arrangements, and the second transfer function can be associated with another one of the optical arrangements. The first transfer function and the second transfer function can be associated with the same optical arrangement of the optical arrangement(s) so as to facilitate different illuminations of the same optical arrangement. The optical arrangement(s) can be configured to be illuminated by a ring-shaped beam.

In yet a further exemplary embodiment of the present disclosure, the optical arrangement(s) can be configured to be illuminated by a ring-shaped beam which has a plurality of rings which include at least one of diameters or thicknesses that are different from one another. The first transfer function and/or the second transfer function of the optical element(s) can be changed using a spatial modulating arrangement. The spatial modulating arrangement can include a masking arrangement, a digital light processor, an apodizer and/or a deformable mirror arrangement. The optical arrangement(s) can include at least one axicon lens arrangement. The data can be generated by (i) utilizing information associated with the first transfer function and/or the second transfer function, or (ii) filtering or scaling information associated with the first transfer function and/or the second transfer function.

According to a still further exemplary embodiment, an interferometric arrangement can include at plurality of detectors, and each of the detectors can be configured to detect the first transfer function and the second transfer function. The interferometric arrangement can include a common-path interferometer, and the common-path interferometer can include a masking arrangement or an apodizing arrangement. A switching arrangement can be provided which is configured to switch an illumination of (i) the first radiation or the third radiation, or (ii) the second radiation or the fourth radiation. A multiplexing arrangement can also be provided which is configured to arrange an illumination of (i) the first radiation and the third radiation, or (ii) the second radiation and the fourth radiation with respect to time, wavelength or coherence length. At least one further processing arrangement can be provided which is configured to generate the data by utilizing the first transfer function and/or the second transfer function.

These and other objects, features and advantages of the exemplary embodiment of the present disclosure will become apparent upon reading the following detailed description of the exemplary embodiments of the present disclosure, when taken in conjunction with the appended claims.

BRIEF DESCRIPTION OF THE DRAWING(S)

Further objects, features and advantages of the present invention will become apparent from the following detailed description taken in conjunction with the accompanying figures showing illustrative embodiments of the present disclosure, in which:

FIG. 4 is a side cut-away view of a diagram of the distal optics of a OCT catheter system according to an exemplary embodiment of the present disclosure;

FIG. 5A is an exemplary graph of an illumination profile generated using the distal optics configuration of the system the exemplary embodiment of shown in FIG. 4;

FIG. 5B is an exemplary graph of simulated x-z PSF generated using the distal optics configuration of the system the exemplary embodiment of shown in FIG. 4;

FIG. 8 is a side cut-away view of a diagram of the OCT catheter system according to yet further exemplary embodiment of the present disclosure which includes an exemplary optical pathlength incoding probe configuration that uses a single fiber and a single axicon lens;

FIG. 14A is an illustration of a Huygens diffraction pattern of lens with conventional focusing;

FIG. 14B is an exemplary illustration of a Huygens diffraction pattern of lens with reflective achromatic phase mask and ball lens depicted in the exemplary embodiment of the system illustrated in FIG. 13.

FIG. 15A is a schematic diagram of an exemplary embodiment of a focusing arrangement that uses a refractive achromatic phase doublet mask in accordance with an exemplary embodiment of the present disclosure;

FIG. 15B is an exemplary graph of transverse phase profiles of an exemplary mask illustrated in FIG. 15A;

FIG. 18A is an exemplary μOCT image of a coronary plaque showing multiple leukocytes (arrows);

FIG. 18B is an exemplary μOCT image of a coronary plaque illustrating multiple leukocytes (arrows) of two different cell types, one smaller cell with scant cytoplasm, consistent with a lymphocyte (L) and another, larger cell with a highly scattering cytoplasm, indicative of a monocyte (M);

FIG. 18C is an exemplary μOCT image of a coronary plaque illustrating a cell with an indented, bean-shaped nucleus (M) characteristic of a monocyte;

FIG. 18D is an exemplary μOCT image of a coronary plaque illustrating a leukocyte with a multi-lobed nucleus, which can indicate a neutrophil (N) attached to the endothelial surface;

FIG. 18E is an exemplary μOCT image of the coronary plaque illustrating multiple leukocytes tethered to the endothelial surface by pseudopodia;

FIG. 18F is an exemplary μOCT image of the coronary plaque illustrating cells with the morphology of monocytes (M) in a cross-section and an inset transmigrating through the endothelium;

FIG. 18G is an exemplary μOCT image of multiple leukocytes distributed on the endothelial surface;

FIG. 19A is an exemplary μOCT image of platelets (P) adjacent to a leukocyte characteristic of a neutrophil (N), which is also attached to a small platelet;

FIG. 19B is an exemplary μOCT image of fibrin (F) which is visible as linear strands bridging a gap in the coronary artery wall;

FIG. 19C is an exemplary μOCT image of a cluster of leukocytes (L), adherent to the fibrin in an adjacent site to that illustrated in FIG. 19B;

FIG. 19D is an exemplary μOCT image of Fibrin thrombus (T) with multiple, entrapped leukocytes;

FIG. 19E is an exemplary μOCT image of a more advanced thrombus (T) showing a leukocyte and fibrin strands (see inset, FIG. 19F);

FIG. 22A is an exemplary μOCT image of a large calcium nodule, demonstrating disrupted intima/endothelium;

FIG. 22B is an expanded view of the region enclosed by a box illustrating microscopic tissue strands, consistent with fibrin (F), adjoining the unprotected calcium (white arrow) to the opposing detached intima;

FIG. 22C is an illustration of a corresponding histology of fibrin (F, black arrows) and denuded calcific surface (gray arrow);

FIG. 27B is a flow diagram of the process according to another exemplary embodiment of the present disclosure.

Figure 1:
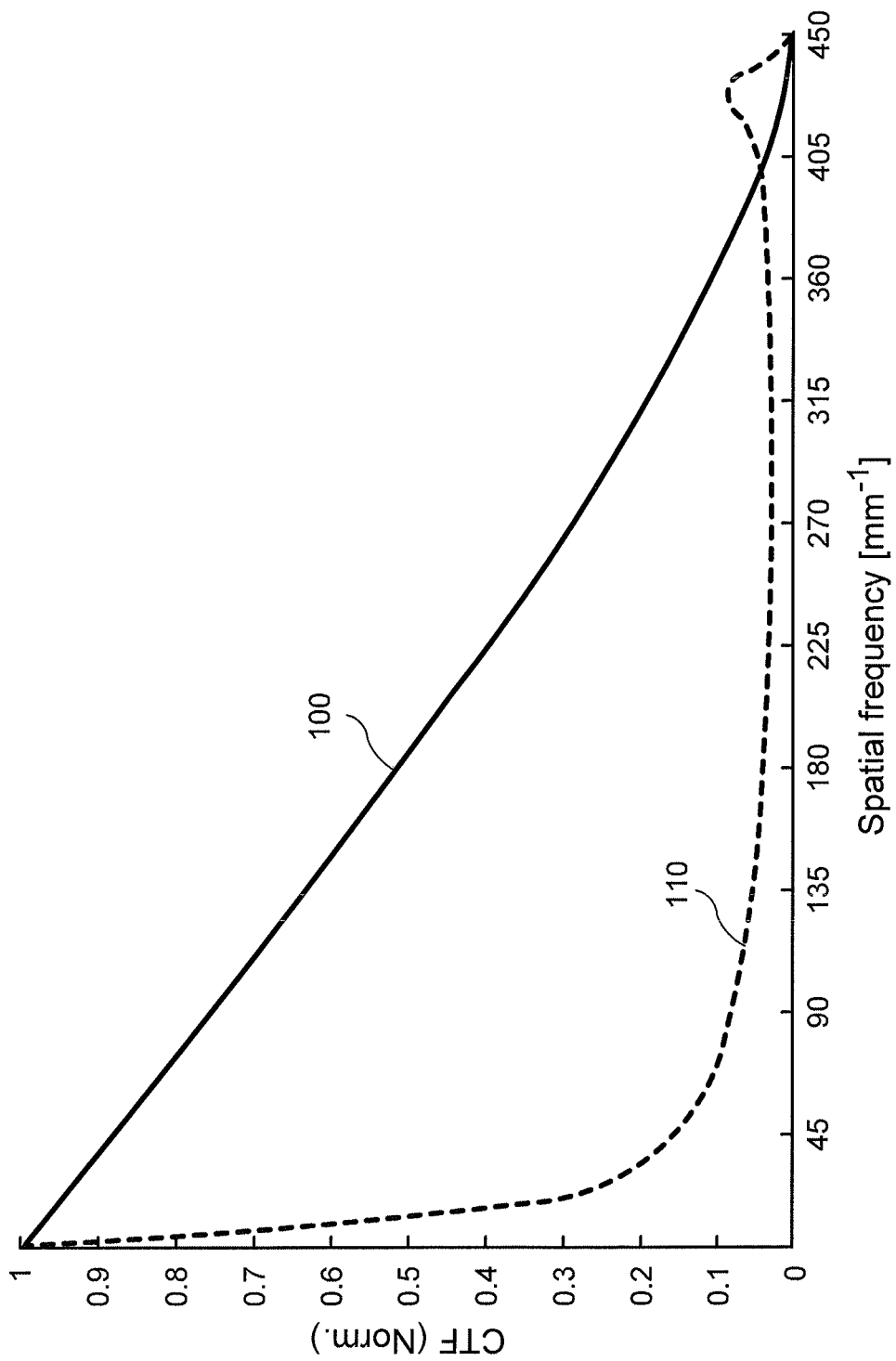
FIG. 1 is an exemplary graph of coherent transfer functions (CTFs) as a function of spatial frequencies produced by the prior Bessel beam illumination and detection.

Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative embodiments. It is intended that changes and modifications can be made to the described exemplary embodiments without departing from the true scope and spirit of the subject disclosure as defined by the appended claims.

DETAILED DESCRIPTION OF EXEMPLARY EMBODIMENTS

According to one exemplary embodiment of the present disclosure, two or more imaging channels can be utilized, e.g., at least one which providing the Bessel beam illumination or detection and at least another one of which providing a Gaussian beam illumination or detection. This exemplary configuration can facilitate three or more unique and separable illumination-detection combinations (e.g., Bessel-Bessel, Bessel-Gaussian, Gaussian-Gaussian, etc.), where each combination can correspond to a different OCT image. As shown in the exemplary graph of FIG. 2, coherent transfer functions (CTFs) for 2.5 μm diameter spots are provided.

Figure 2:
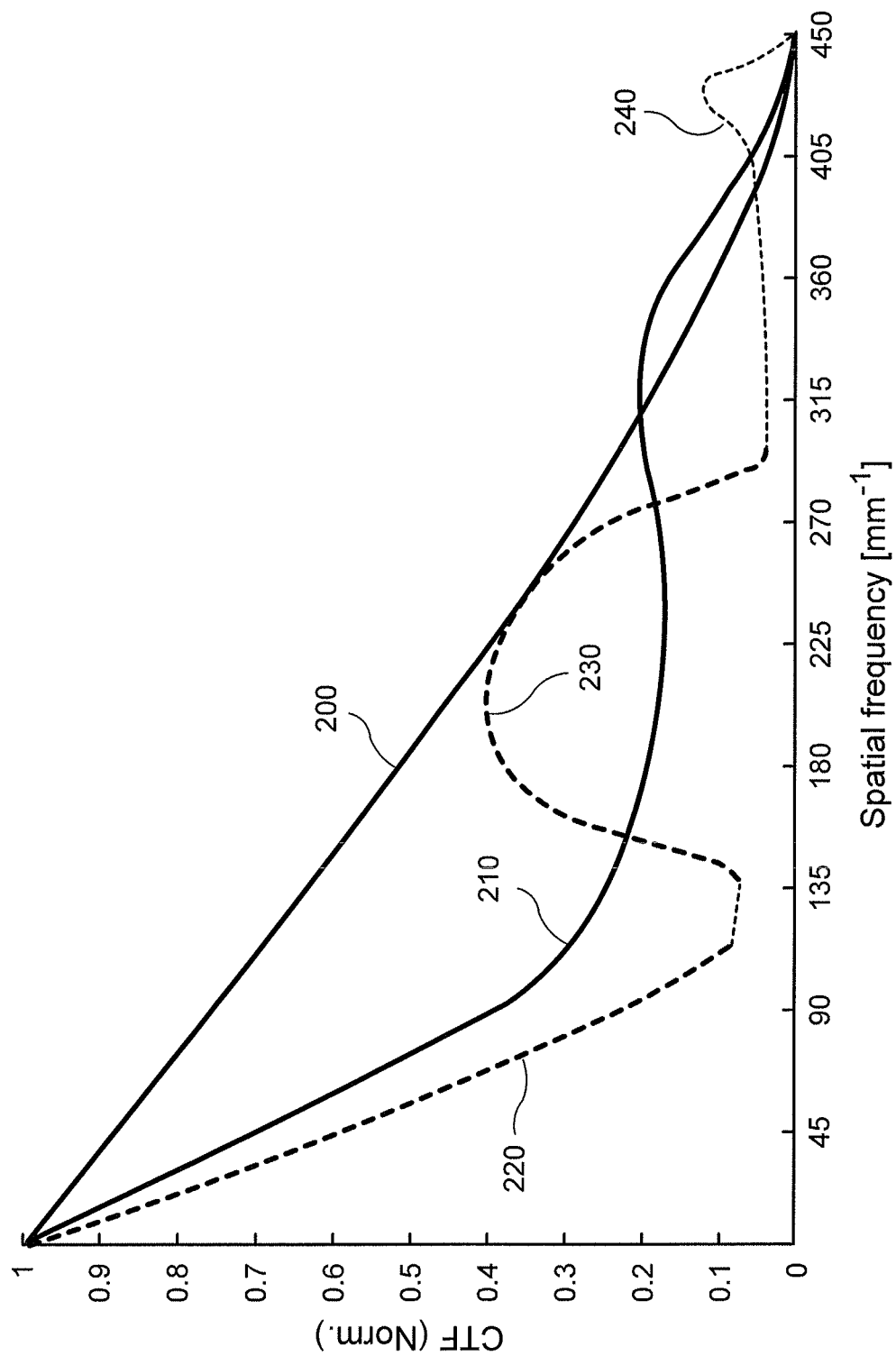
FIG. 2 is an exemplary graph of coherent transfer functions (CTFs) as a function of spatial frequencies produced by an exemplary embodiment of a procedure and/or technique according to the present disclosure.

For example, FIG. 2 illustrates a graphical comparison of a diffraction limit 200, extended focal range of 0.15 mm used in preliminary data 210, and the exemplary results of an exemplary embodiment of a procedure or technique according to the present disclosure, hereinafter termed μOCT, with a focal range of 2.0 mm. According to one exemplary embodiment of the present disclosure he μOCT CTF can be generated, e.g., by combining Gaussian-Gaussian images 220, Bessel-Gaussian images 230, and Bessel-Bessel images 240.

In another exemplary embodiment of the present disclosure, the exemplary μOCT CTF procedure/technique can be used and/or provided over an axial focus range that can be, e.g., more than 0.5 mm, 1 mm, 2 mm, etc. (as well as others). According to additional exemplary embodiments of the present disclosure, the transverse FWHM spot diameters can be less than 5 μm, 2 μm, 1 μm, etc. (as well as others). In still further exemplary embodiments of the present disclosure, the depth of focus can be extended a factor of, e.g., approximately 2, 5, 10, 20, 50, 100, etc. (and possibly more) compared to the illumination with a plane wave or Gaussian beam. In yet another exemplary embodiment of the present disclosure, the high, low, and medium spatial frequency content in the image can be at least partially restored by combining images with different transfer functions.

Figure 3A:
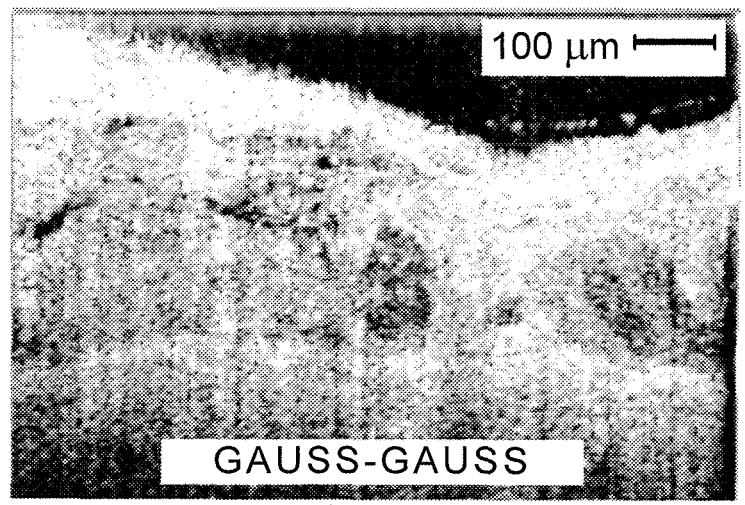
FIG. 3A is a first exemplary OCT image an exemplary OCT image of a cadaver coronary artery plaque obtained using an exemplary procedure/techniques according to an exemplary embodiment of the present disclosure, whereas an exemplary Gauss-Gauss image contains low spatial frequency information.
Figure 3B:
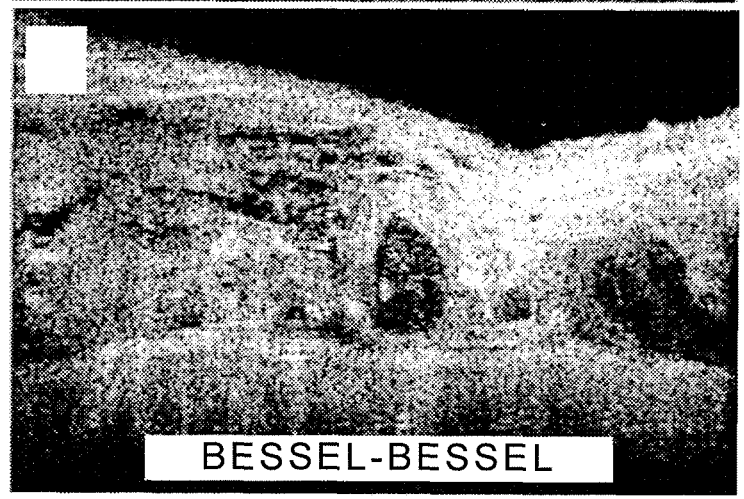
FIG. 3B is a second exemplary OCT image of the cadaver coronary artery plaque using an exemplary procedure/techniques according to an exemplary embodiment of the present disclosure, whereas an exemplary Bessel-Bessel image provides high-resolution but loses low and mid spatial frequencies.
Figure 3C:
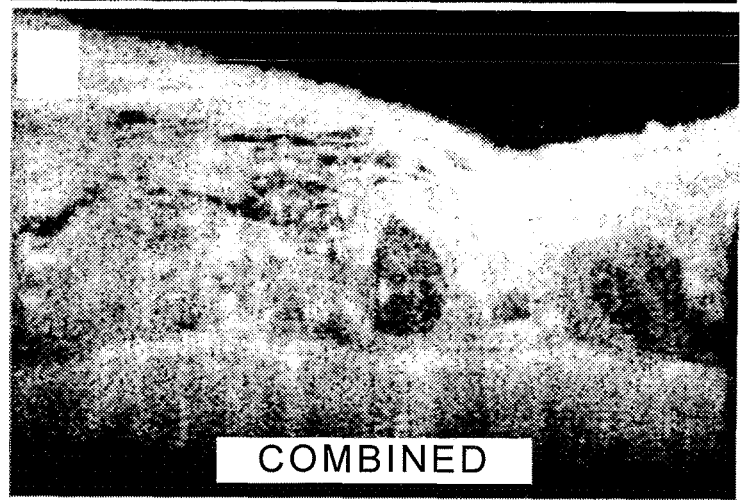
FIG. 3C is a third exemplary OCT image of the cadaver coronary artery plaque using an exemplary procedure/techniques according to an exemplary embodiment of the present disclosure, which provides a combined μOCT image (e.g., Gauss-Gauss+Gauss-Bessel+Bessel-Bessel), and images are normalized and displayed with the same brightness/contrast values.

FIGS. 3A-3C show exemplary OCT images of a cadaver coronary artery plaque obtained using an exemplary procedure/techniques according to exemplary embodiments of the present disclosure. For example, in FIG. 3A an exemplary Gauss-Gauss image contains low spatial frequency information. In FIG. 3B, an exemplary Bessel-Bessel image provides high-resolution but loses low and mid spatial frequencies. Further, in FIG. 3C, a combined μOCT image (e.g., Gauss-Gauss+Gauss-Bessel+Bessel-Bessel) is provided, and images are normalized and displayed with the same brightness/contrast values.

FIG. 4 shows a second exemplary embodiment of distal optics of a OCT catheter system according to the present disclosure. For example, the exemplary system of FIG. 4 illustrates an axicon arrangement (e.g., pair) and a routing of the annulus (shown in a darker shade in FIG. 4) and the Gaussian beam (shown in a darker shade in FIG. 4) of the distal optics design according to this exemplary embodiment. In particular, the exemplary system illustrate din FIG. 4 can generate a diffraction-limited CTF and an axial focus range (e.g., depth-of-focus) that can be more than, e.g., 10 times longer than the diffraction-limited depth-of-focus. The output of a waveguide 500 can be collimated by a collimator 510 located in a center of the exemplary catheter system. The collimated electro-magnetic radiation (e.g., light) can be transformed into an annular beam using two or more axicons 520, 530. According to another exemplary embodiment, the axicons can be generated or produced using gradient index.

As shown in FIG. 4, a separate waveguide 540 can be routed through the center of the annulus. The output of the waveguide can be collimated by a collimator 550 located in the center of the annulus. Simulated transverse intensity profiles of the collimated annular and Gaussian beams are shown in an illustration of FIG. 5A. Collimated annular and Gaussian beams can be focused onto the sample using one or more lens, such as a GRIN lens 560. In addition to focusing two or more beams, the GRIN lens 560 can be configured to intentionally generate chromatic aberration, which can extend the axial focus further (as shown in an illustration of FIG. 5B), and to compensate the aberrations induced by the transparent outer sheath 570. The electro-magnetic radiation (e.g., light) can be directed to the artery wall by a deflector 580.

Figure 6:
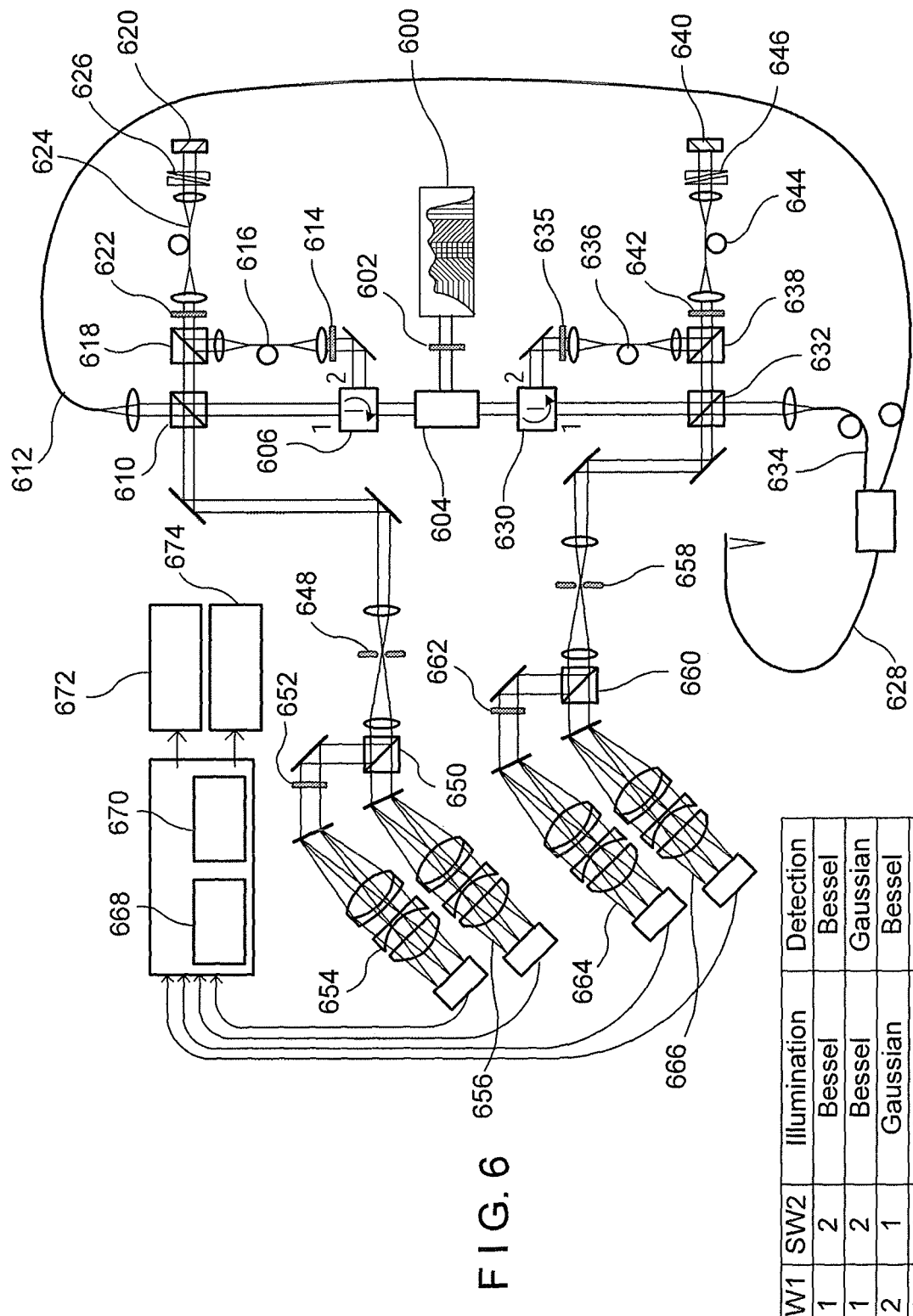
FIG. 6 is a schematic diagram of a system for generating one or more μOCT images according to still a further exemplary embodiment of the present disclosure.

FIG. 6 shows a schematic diagram of an imaging system for generating μOCT images according to an exemplary embodiment of the present disclosure. As provided in the exemplary embodiment of FIG. 6, an output of a source 600 providing electro-magnetic radiation(s) (e.g., light radiation) can be linearly polarized by a linear polarizer 602, and split into two or more beams by a beam splitter 604. At least one of the beams can be redirected to an input port of a switch 606.

At least one of outputs of the switch 606 can be transmitted through a beam splitter 610, and coupled into a first light/electro-magnetic radiation guide 612. Another other of the outputs of the switch 606 can be attenuated by an attenuator 614, guided by a second light/electro-magnetic radiation guide 616 to a third beam splitter 618, and redirected to a reference reflector 620 through an attenuator 622, a third light/electro-magnetic radiation guide 624 and a dispersion compensation arrangement 626. An output of the light guide 612 can be connected to Bessel illumination and Bessel detection channel of a catheter 628.

As shown in FIG. 6, a further one of the outputs of the beam splitter 604 can be redirected to input port of a second three-port switch 630. One of the outputs of the switch 630 can be transmitted through a beam splitter 632, and coupled into a fourth light/electro-magnetic radiation guide 634. Another one of the outputs of the switch 630 can be attenuated by an attenuator 635 guided by a fifth light guide 636 to a fourth beam splitter 638, and redirected to a reference reflector 640 through an attenuator 642, a fifth light guide 644 and a second dispersion compensation arrangement 646. The output of the light guide 634 can be connected to a Gaussian illumination and Gaussian detection channel of the catheter 628.

When the state of the switch 606 is 1, and the state of a fourth beam splitter 638 is 2, e.g., only the light/electro-magnetic radiation guide 612 can be illuminated so that the sample is illuminated by the Bessel illumination channel (see Table 1 of FIG. 6). The back-scattered light from the sample can picked up by both, some or all of the Bessel and Gaussian detection channels of the catheter 628 (see Table 1 of FIG. 6). The portion of electro-magnetic radiation/light picked up by the Bessel detection channel can be guided by the first electro-magnetic radiation/light guide 612 to the beam splitter 610, where such radiation/light can be combined and interfered with the light from the reference reflector 620.

Further, as illustrated in FIG. 6, at least part of the interference signal can be directed by the beam splitter 610 to a pinhole 648. An output of the pinhole 648 can be collimated and split by a polarizing beam splitter 650. One of outputs of the polarizing beam splitters 650 can be transmitted through a half wave plate 652, and detected by a spectrometer 654. Another of the outputs of the polarizing beam splitters 650 can be detected by a second spectrometer 656. A portion of the electro-magnetic radiation/light picked up by the Gaussian detection channel can be guided by the light guide 634 to the beam splitter 632, where it is combined and interfered with the light from the reference reflector 640. At least part of the interference signal can be directed by the beam splitter 634 to a pinhole 658. An output of the pinhole 658 can be collimated and split by a polarizing beam splitter 660. At least one of outputs of the polarizing beam splitters 660 can be transmitted through a half wave plate 662, and detected by a third spectrometer 664. Another of the outputs of the polarizing beam splitters 660 can be detected by a fourth spectrometer 666.

When the state of the switch 606 is 2 and the state of the switch 638 is 1, e.g., only the fourth electro-magnetic radiation/light guide 634 can be illuminated, so that the sample is illuminated by Gaussian illumination channel (shown in Table 1 of FIG. 6). The back-scattered electro-magnetic radiation/light from the sample can be picked up by both Bessel and Gaussian detection channels of the catheter 630 (shown in Table 1 of FIG. 6). At least one portion of the electro-magnetic radiation/light picked up by the Bessel detection channel is guided by the electro-magnetic radiation/light guide 612 to the beam splitter 610, where it can be combined and interfered with the light from the reference reflector 620. At least part of the interference signal can be directed by the beam splitter 610 to a pinhole 648. An output of the pinhole 648 can be collimated and split by a polarizing beam splitter 650. At least one of outputs of the polarizing beam splitters 650 can be transmitted through a half wave plate 652, and detected by a spectrometer 654. Another of the outputs of the polarizing beam splitters 650 can be detected by a second spectrometer 656.

The portion of light picked up by the Gaussian detection channel is guided by the electro-magnetic radiation/light guide 634 to the beam splitter 632, where it is combined and interfere with the light/radiation from the reference reflector 640. At least part of the interference signal can be directed by the fourth electro-magnetic radiation/light guide 634 to a pinhole 658. The output of pinhole 658 is collimated and split by a polarizing beam splitter 660. AT least one of the two outputs of the polarizing beam splitters 660 can be transmitted through a half wave plate 662, and detected by a third spectrometer 664. Another of the outputs of the polarizing beam splitters 660 can be detected by a fourth spectrometer 666.

Such exemplary polarization-diverse detection scheme/configuration shown in FIG. 6 implemented by the combination of the polarizing beam splitter 650, the half wave plate 652 and the spectrometers 654, 656, and/or a combination of the polarizing beam splitter 660, the half wave plate 662 and the spectrometers 664, 666 can reduce and/or eliminate artifacts associated with tissue or optical fiber birefringence. The exemplary embodiment of the μOCT catheter system according the present disclosure illustrated in FIG. 6 can contain multiple waveguides that can, e.g., independently transmit and/or receive light/radiation from the catheter to waveguides 612 and 632. The detected signal can be digitized and transferred by a computer 668 via an image acquisition board 670. Data can be digitally displayed on or via a monitor 672, and/or stored in a storage device 674.

According the present disclosure, the µOCT detection technology can be implemented using, in one exemplary embodiment, a time domain OCT (TD-OCT) system, in another exemplary embodiment, a spectral-domain (SD-OCT) system, and, in yet another exemplary embodiment, an optical frequency domain interferometry (OFDI) system. Complex images and/or real images from the different transfer function illumination and detection configurations can be acquired using the exemplary embodiment of the imaging system according to the present disclosure. In one exemplary embodiment, such exemplary images can be filtered and recombined to generate a new image with an improved quality and a CTF that more closely approximates the diffraction limited CTF. The exemplary images with different transfer functions can be filtered or recombined incoherently and/or coherently to generate a new image with a CTF procedure/technique that more closely approximates the diffraction limited CTF procedure/technique.

Figure 7:
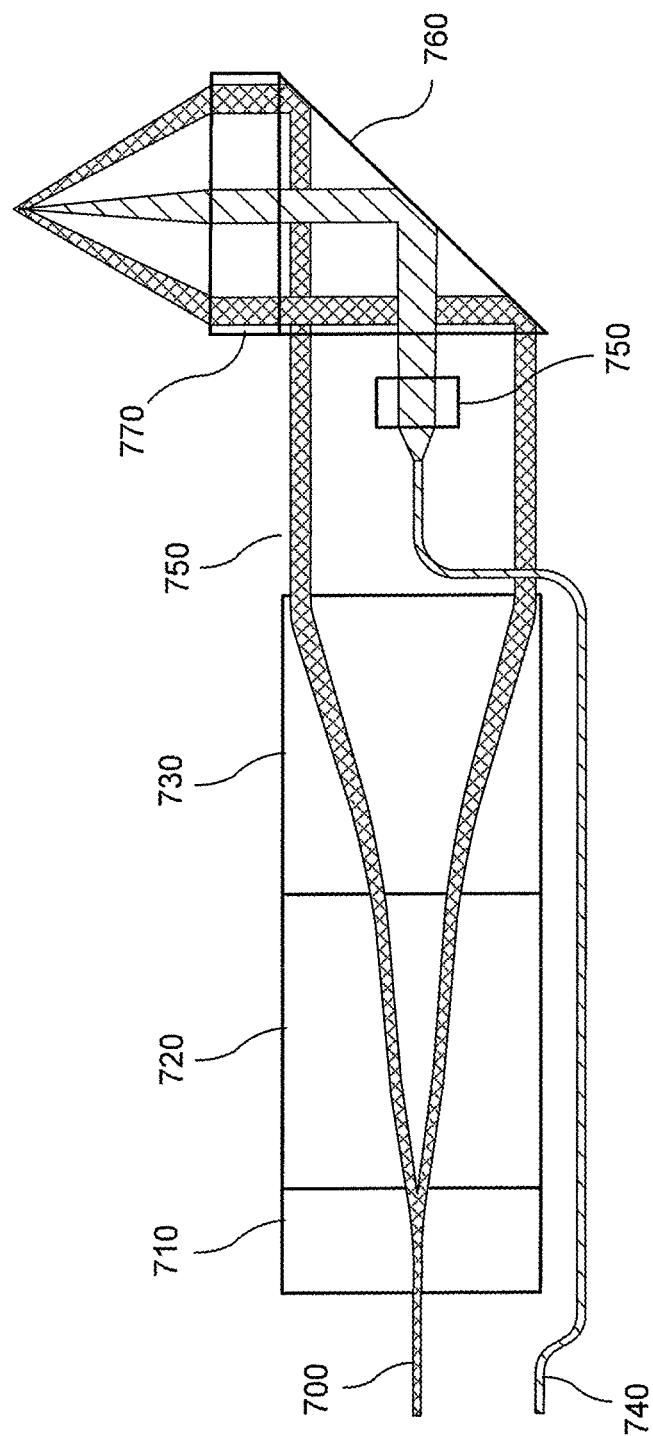
FIG. 7 are side cut-away views of diagrams of the distal optics of the OCT catheter system according to still another exemplary embodiment of the present disclosure which includes axicon pair and a routing of a ring beam and a Gaussian beam of the distal optics configuration.

FIG. 7 shows another exemplary embodiment of distal optics configuration of a OCT catheter according to the present disclosure for generating a diffraction-limited CTF and an axial focus range (e.g., depth-of-focus) that can be more than, e.g., approximately 10 times longer than the diffraction-limited depth-of-focus.

For example, an output of a waveguide 700 can be collimated by a collimator 710. Indeed, the waveguide 700 can be routed through the annular beam and is collimated Gaussian beam will be routed through the center of the annulus. The collimated light can be transformed into an annular beam through two or more axicons, such as, e.g., GRIN axicons 720, 730. A separate waveguide 740 can be routed through a center of the annulus. An output of the waveguide 740 can be collimated by a collimator 750 located in the center of the annulus. The collimated annular and Gaussian beams can be focused onto the sample using one or more lens(es) 770, which can be, e.g., one or more GRIN lenses. In addition to focusing the beams, the GRIN lens 770 can be configured and/or structured to intentionally generate chromatic aberration(s), which can extend the axial focus further and compensate for the aberrations induced by a transparent outer sheath. The light/radiation can be directed to the artery wall by a deflector 760.

FIG. 8 shows another exemplary embodiment of the distal optics configuration of the OCT catheter according to the present disclosure. Such exemplary configuration can be used to generate a diffraction-limited CTF and depth of focus that is, e.g., more than 10 times longer than the diffraction-limited depth-of-focus. An output of a waveguide 800 can be collimated by a collimator 810. A pupil aperture created by the collimator 810 can be split into two or more beams, i.e., central circular beam(s) and an annular beam. One or more lenses 820, such as an objective lens, achromat lens, aplanat lens, or GRIN lens, that has an aperture substantially the similar as or identical to a central zone can focus a low NA Gaussian beam into the tissue or the sample.

The annular beam can be transmitted through a spacer 830, and focused into the sample by an annular axicon lens 840 with an aperture that is substantially similar or identical to the annular beam. The beams can be directed to the sample by a deflector 850. There can be 20 four images generated from four channels, e.g., central illumination/central detection, central illumination/annular detection, annular illumination/annular detection, annular illumination/central detection. The optical pathlength of the lens 820 can be configured to be different from that of the spacer 830 so that each of, e.g., four images generated can be pathlength encoded. In this exemplary embodiment, the different images can be detected, and their CTF can be combined as per the exemplary methods and/or procedures described herein.

Figure 9:
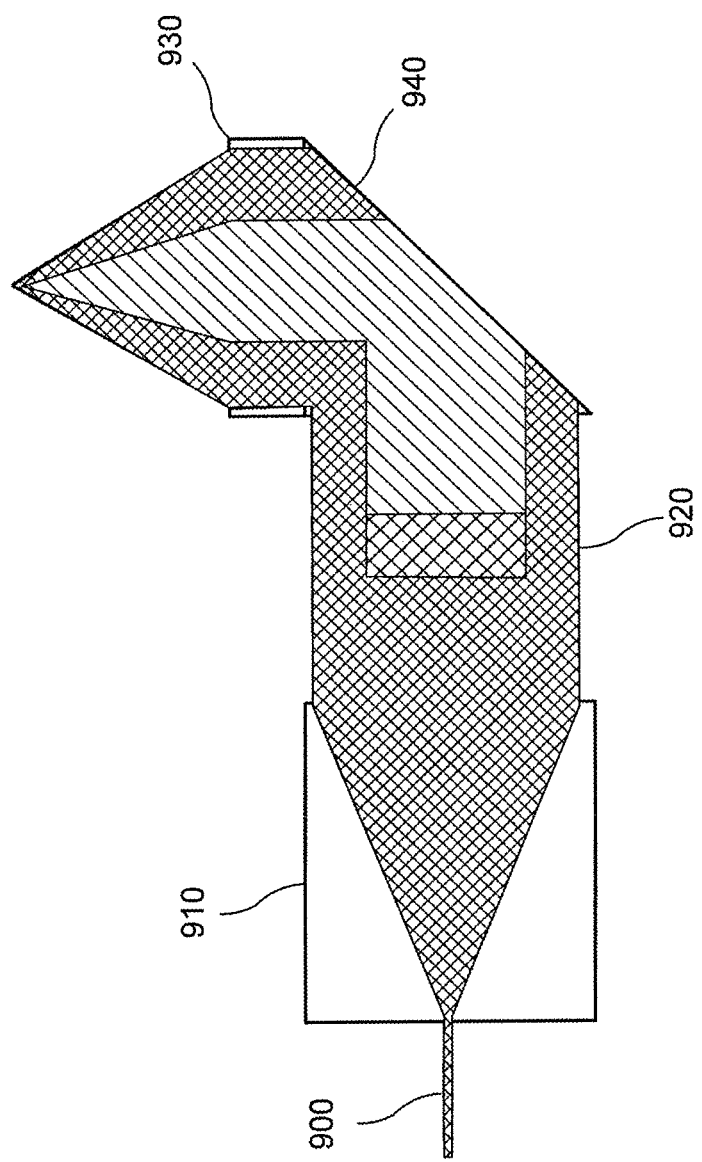
FIG. 9 are side cut-away views of diagrams of the OCT catheter system according to a still further exemplary embodiment of the present disclosure which includes a further exemplary optical pathlength incoding probe configuration that uses a single fiber and a single axicon lens.

FIG. 9 shows another exemplary embodiment of the distal optics configuration of the OCT catheter system according to the present disclosure, which can be used for generating a diffraction-limited CTF and a depth of focus that is longer than the diffraction-limited depth-of-focus. For example, as illustrated in FIG. 9, the output of a waveguide 900 can be collimated by a collimator 910. A pupil aperture created by the collimator 910 can be split into two or more zones by a circular glass window 920 positioned at the center of the objective lens aperture, e.g., (i) a central circular zone that is transmitted through the circular glass window 920, and (ii) an annular zone. The central circular beam can be focused as a low NA Gaussian beam into the tissue and/or sample, and the annular beam can be focused into a Bessel beam focus in the tissue by the lens 930. A glass window can have a higher refractive index than air, and the thickness of the window can be so chosen such that the light/radiation field that undergoes different channel can be path-length separated and/or encoded. In each A line, there can be three or more segments of signal coming from the (e.g., 4) channels: central illumination/central detection, central illumination/annular detection, annular illumination/annular detection, annular illumination/central detection.

Figure 10:
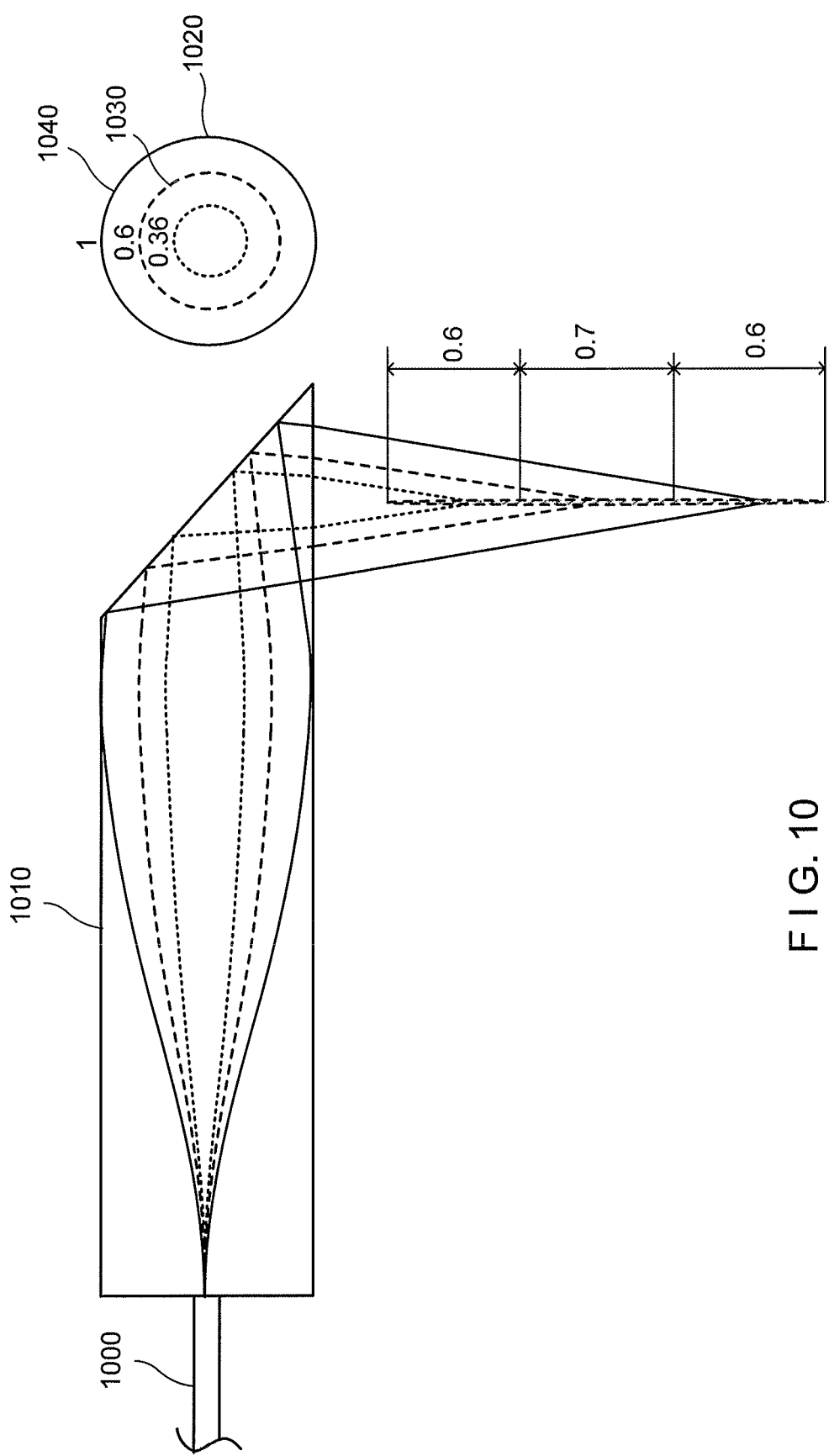
FIG. 10 are schematic views of diagrams of the distal optics of the OCT catheter system according to a further exemplary embodiment of the present disclosure which includes a single fiber multifocal lens probe configuration.

FIG. 10 shows a further exemplary embodiment of the distal optics configuration of the OCT catheter system for generating a diffraction-limited CTF and a depth of focus that can be longer than the diffraction-limited depth-of-focus. An output of a waveguide 1000 can be collimated by a collimator 1010. A pupil aperture created by the collimator 1010 can be split into a number of concentric zones 1020, 1030, 1040. A multifocal lens, such as, e.g., a GRIN lens, can be used so that the beam in each zone can be focused to a different axial focal position. The scattered light/radiation from each zone can be optical pathlength-encoded so that such scattered beams do not interfere with each other. In this exemplary embodiment, the different images can be detected, and their CTF combined pursuant to the exemplary methods and procedures described herein.

Figure 11:
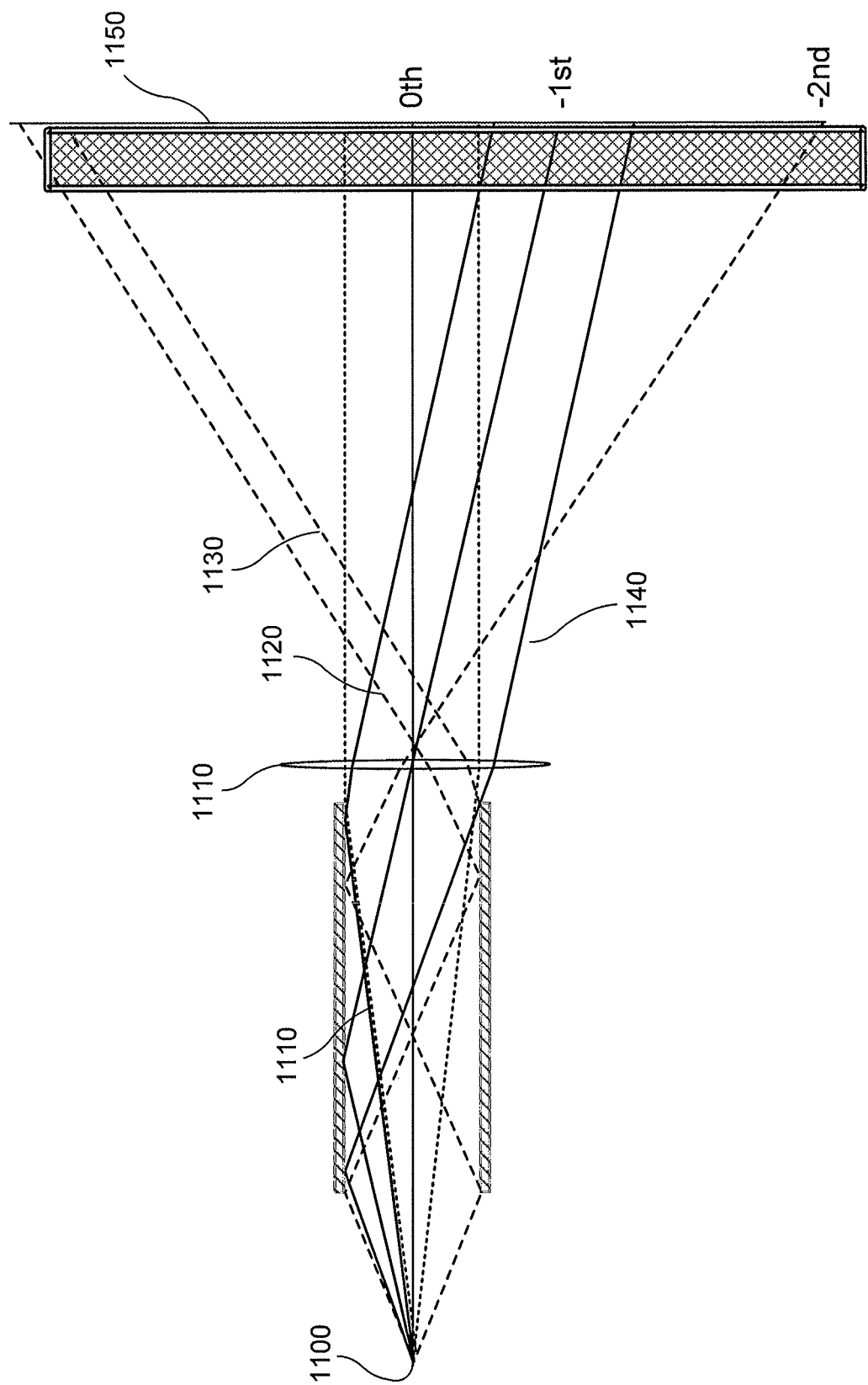
FIG. 11 is a side cut-away view of a diagram of the OCT catheter system according to a still further exemplary embodiment of the present disclosure which utilizes a mirror tunnel.

FIG. 11 shows yet another exemplary embodiment of the distal optics configuration of the OCT catheter system for generating a diffraction-limited CTF and an axial focus range (e.g., depth-of-focus) that is longer than the diffraction-limited depth-of-focus. For example, an output of a point object 1100 can be transformed by a mirror tunnel device 1110 to multiple orders of light/radiation beams, e.g., zeroth order beam 1120, −1st order beam 1130, and −2nd order beam 1140, etc. When a focusing device 1150 is employed so that most or all the order of rays are focused at the same focal position in the sample, each order of rays can contain a unique band of spatial frequency of the illumination/detection CTF of the focusing device. These orders can, in yet another exemplary embodiment, be path length-encoded so that images generated therein can be detected, and their CTF combined using the different images corresponding to the different orders as per the exemplary CTF combination methods and/or procedures described herein.

Figure 12:
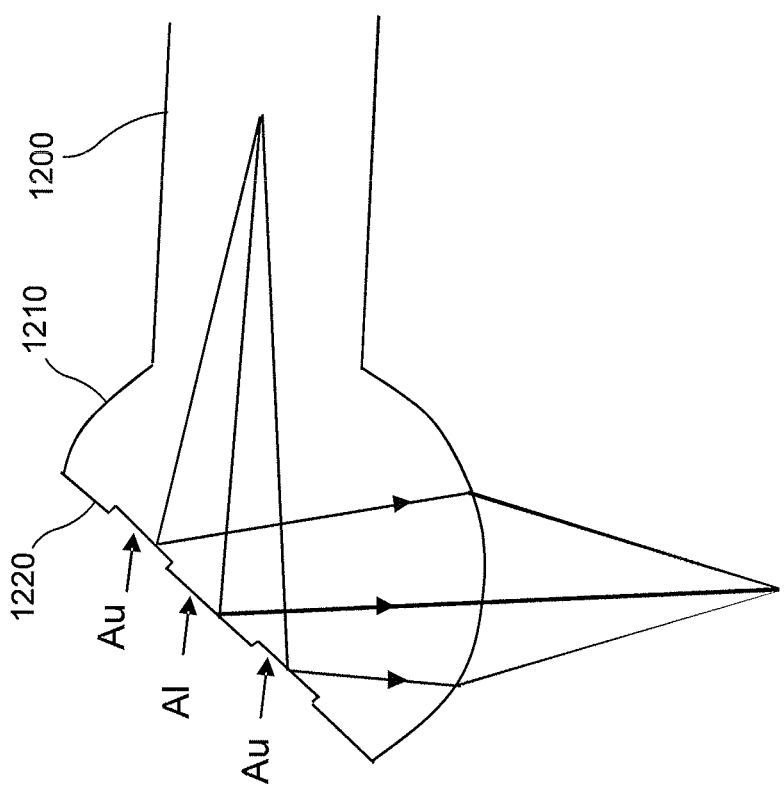
FIG. 12 is a side cut-away view of a diagram a portion of the OCT catheter system according to yet another exemplary embodiment of the present disclosure which utilizes a reflective achromatic phase mask and a ball lens.

FIG. 12 shows another exemplary embodiment of the distal optics configuration of the OCT catheter system according to the present disclosure for generating a diffraction-limited CTF and a depth of focus that is longer than the diffraction-limited depth-of-focus. As illustrated in FIG. 12, an output of a waveguide 1200 can be focused by a half ball lens 1210. A planar surface of the half ball lens 1210 can have a binary phase pattern 1220. In one further exemplary embodiment, the depth of the pattern can be configured to produce a small phase shift, e.g., such as a pattern depth of 198 nm (n phase shift at 850 nm). In another exemplary embodiment, the top surface can be coated with a reflecting coating, such as Au, and a bottom surface can be coated with the same and/or another coating such as Al, with the final phase shift being given by a curve 1300 shown in a graph of FIG. 13, which illustrates an optical phase length difference of the glass mask (e.g., no metal coating) and a total phase shift (e.g., mask+coating).

Figure 13:
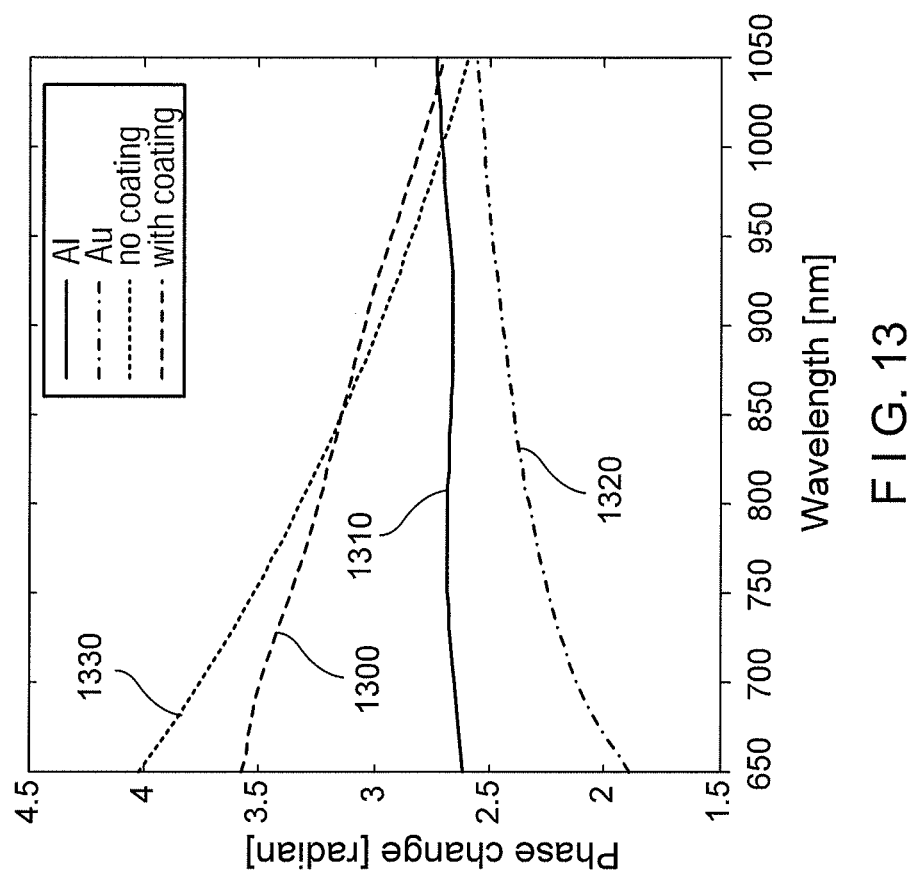
FIG. 13 is a graph of a phase shift spectra of chromatic light upon reflection at glass-metal interface based on the exemplary embodiment of FIG. 12.

A curve 1310 and a curve 1320 of the graph of FIG. 13 can have a wavelength-dependent phase change of the p-polarized light upon reflection at BK7-Al and BK7-Au, respectively, with an incident angle of 45 degrees. The curve 1330 can be the wavelength dependent phase shift of the light caused by, e.g., 198 nm height difference upon 45 degree reflection at BK7-air interface. A binary phase mask can be optimized to produce an extended axial focus (as shown in an illustration of FIG. 14b) compared with the diffraction limited axial focus (as shown in an illustration of FIG. 14a). The light/radiation transmitted from the surfaces with different phase shifts can generate different transfer functions, which can be detected and combined to create a new image with a different CTF pursuant to the exemplary methods and/or procedures described herein.

FIG. 15A shows a side-cut-away view of a diagram of another exemplary embodiment of the distal optics configuration of the OCT catheter system for generating a diffraction-limited CTF and an depth of focus longer than the diffraction-limited depth-of-focus. For example, the system of FIG. 15A generates the results by a factor of, e.g., approximately 2, 5, 10, 20, 10, 100, etc. An output of a waveguide 1500 can be collimated by one or more lens(es) 1510. The collimated beam can be spatially modulated by a phase doublet 1520, which can include a positive phase plate and a negative phase plate with the same or similar phase pattern. By matching Abbe number of the positive phase plate and the negative phase plate, the wavelength dependent phase error can be canceled or reduced. FIG. 15B shows an exemplary graph of transverse phase profiles of an exemplary mask (e.g., BK7-SNPH2 phase doublet mask) illustrated in FIG. 15A For example, by choosing Ohara S-NPH2 (Vd=18.896912, Nd=1.922860) and Schott BK7 (Vd=64.167336, Nd=1.5168), with depth 7.2554 um and 13.4668 um respectively, the phase profile is shown in FIG. 15B. The spatially modulated beam can be focused into an extended axial focus by an objective lens 1530.

Figure 16:
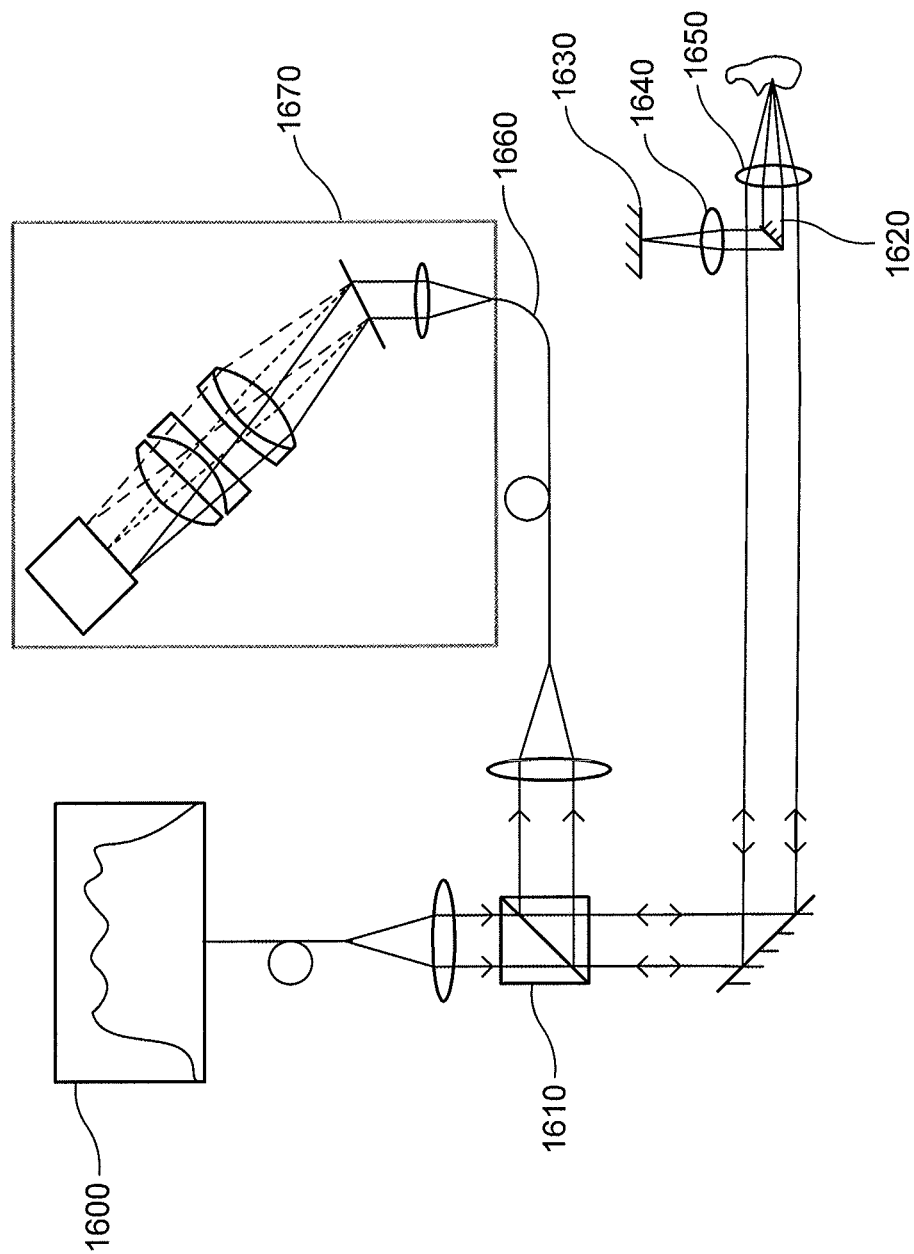
FIG. 16 is a schematic diagram of the OCT system which includes a wavefront beam splitter and a common path interferometer, according to yet another exemplary embodiment of the present disclosure.
Figures 17A, 17B:
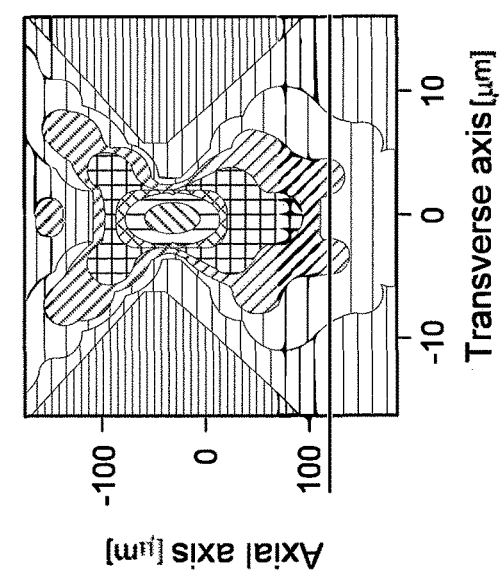
FIG. 17A is an exemplary simulated PSF illustration of generated by the exemplary OCT system shown in FIG. 16 that uses a monochromatic light source (e.g., λ=825 nm) and a spherical aberration free objective lens.
FIG. 17B is an exemplary simulated PSF illustration of generated by the exemplary OCT system shown in FIG. 16 that uses a monochromatic light source (e.g., λ=825 nm) and an objective lens with a spherical aberration and a wavelength dependent focal shift.
Figures 17C, 17D:
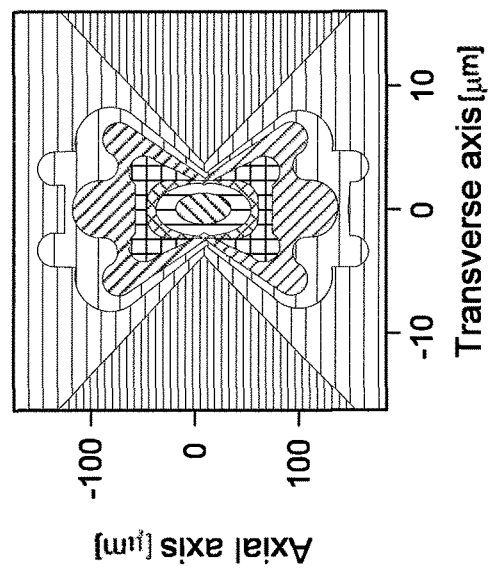
FIG. 17C is an exemplary simulated PSF illustration of generated by the exemplary OCT system shown in FIG. 16 that uses a broadband source (e.g., about 600 nm to 1050 nm) and an objective lens with spherical aberration and a wavelength dependent focal shift.
FIG. 17D is an exemplary simulated PSF illustration of generated by the exemplary OCT system shown in FIG. 16 that uses broadband source (e.g., 600 nm to 1050 nm), an objective lens with spherical aberration and a wavelength dependent focal shift, and an wavefront beam splitter.

FIG. 16 shows still another exemplary embodiment of the distal optics configuration of the OCT catheter system for generating a diffraction-limited CTF and depth of focus according to the present disclosure that is longer than the diffraction-limited depth-of-focus, by a factor of preferably approximately 2, 5, 10, 20, 10, 100, etc. An output of a light source 1600 can be split by a beam splitter 1610. The beam aperture of at least one of the outputs of the beam splitter can be split or separated by a rod mirror 1620 into two or more regions. For example, the rod mirror 1620 can redirect the central part of the beam to a reference reflector 1630 through an objective lens 1640. The annular beam can be focused into the sample by a second objective lens 1660 that can be substantially similar or identical to one or more lens(es) 1640 into a Bessel focus featured with extended axial focus and super-resolution in transverse direction (as shown in the exemplary μOCT images of FIG. 18D). The light back-scattered from the sample is combined with the light reflected from the reference reflector through the rod mirror at a pinhole 1660. The output of the pinhole 1660 is detected by a spectrometer 1670. The objective lens 1650 is configured to intentionally generate chromatic aberration and spherical aberration, which extend the axial focus further (as shown in the exemplary μOCT images of FIGS. 18C and 18D). FIG. 18A shows an exemplary μOCT image of a coronary plaque showing multiple leukocytes (arrows). In addition, FIG. 18B shows an exemplary μOCT image of a coronary plaque illustrating multiple leukocytes (arrows) of two different cell types, one smaller cell with scant cytoplasm, consistent with a lymphocyte (L) and another, larger cell with a highly scattering cytoplasm, indicative of a monocyte (M).

Indeed, FIG. 18A illustrates an exemplary μOCT image of a coronary plaque showing multiple leukocytes 1800 which has been generated using the exemplary embodiment(s) of the methods, systems and apparatus according to the present disclosure. FIG. 18B illustrates an exemplary μOCT image of a coronary plaque showing multiple leukocytes of two different cell types, one smaller cell 1810 with scant cytoplasm, consistent with a lymphocyte and another, larger cell 1820 with a highly scattering cytoplasm, suggestive of a monocyte. FIG. 18C illustrates an exemplary μOCT image of a coronary plaque showing a cell 1830 with an indented, bean-shaped nucleus characteristic of a monocyte. FIG. 18D illustrates an exemplary μOCT image of a coronary plaque showing a leukocyte 1840 with a multi-lobed nucleus, suggestive of a neutrophil attached to the endothelial surface. FIG. 18E illustrates an exemplary μOCT image of a coronary plaque showing multiple leukocytes 1850, tethered to the endothelial surface by pseudopodia 1860. FIG. 18F illustrates an exemplary μOCT image of a coronary plaque showing cells 1870 with the morphology of monocytes in this cross-section and inset transmigrating through the endothelium 1880. Further, FIG. 18G illustrates an exemplary μOCT image of multiple leukocytes 1890 distributed on the endothelial surface.

FIG. 19A-19E show exemplary images which have been generated using the exemplary embodiment(s) of the methods, systems and apparatus according to the present disclosure. For example FIG. 19A illustrates an exemplary μOCT image of platelets 1900 (P) adjacent to a leukocyte characteristic of a neutrophil 1910 (N), which is also attached to a small platelet 1920 (yellow arrow). FIG. 19B illustrates an exemplary μOCT image of fibrin 1930 (F) which is visible as linear strands bridging a gap in the coronary artery wall. FIG. 19C illustrates an exemplary μOCT image of a cluster of leukocytes 1940 (L), adherent to the fibrin in an adjacent site to FIG. 19B. FIG. 19D illustrates an exemplary μOCT image of Fibrin thrombus 1950 (T) with multiple, entrapped leukocytes. FIG. 19E an μOCT image of a more advanced thrombus 1960 (T) showing a leukocyte 1970 (arrow) and fibrin strands 1980 (inset, F).

Figures 20A, 20B, 20C, 20D:
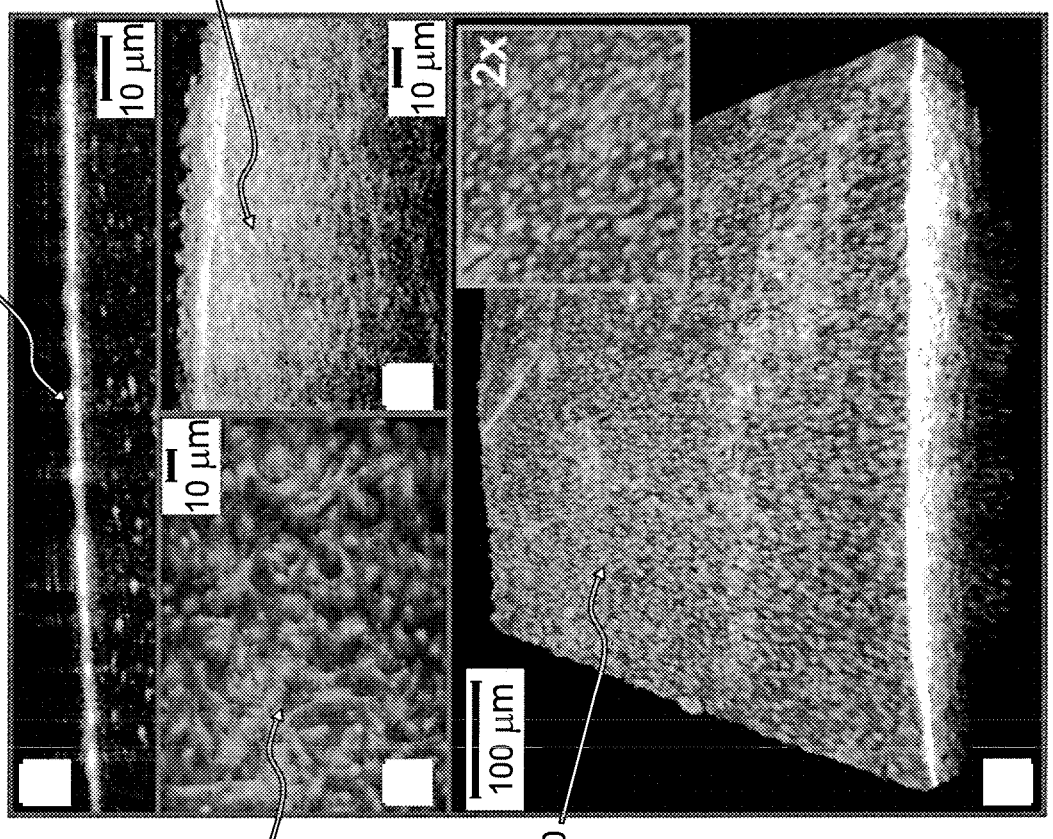
FIG. 20A is a cross-sectional exemplary μOCT image of endothelial cells in culture.
FIG. 20B is an en face exemplary μOCT image of endothelial cells in culture.
FIG. 20C is an exemplary μOCT image of a native swine coronary artery cross-section.
FIG. 20D is an exemplary three-dimensional rendering of the swine coronary artery, demonstrating endothelial "pavementing"

FIGS. 20A-20D show further exemplary images which have been generated using the exemplary embodiment(s) of the methods, systems and apparatus according to the present disclosure. For example, FIG. 20A illustrates a cross-sectional exemplary μOCT image of endothelial cells 2000 in culture. FIG. 20B shows an en face exemplary μOCT image of endothelial cells 2010 in culture. FIG. 20C illustrates an exemplary μOCT image of native swine coronary artery cross-section 2020. FIG. 20D shows a three-dimensional rendering of the swine coronary artery, demonstrating endothelial "pavementing" 2030.

Figures 21A, 21B:
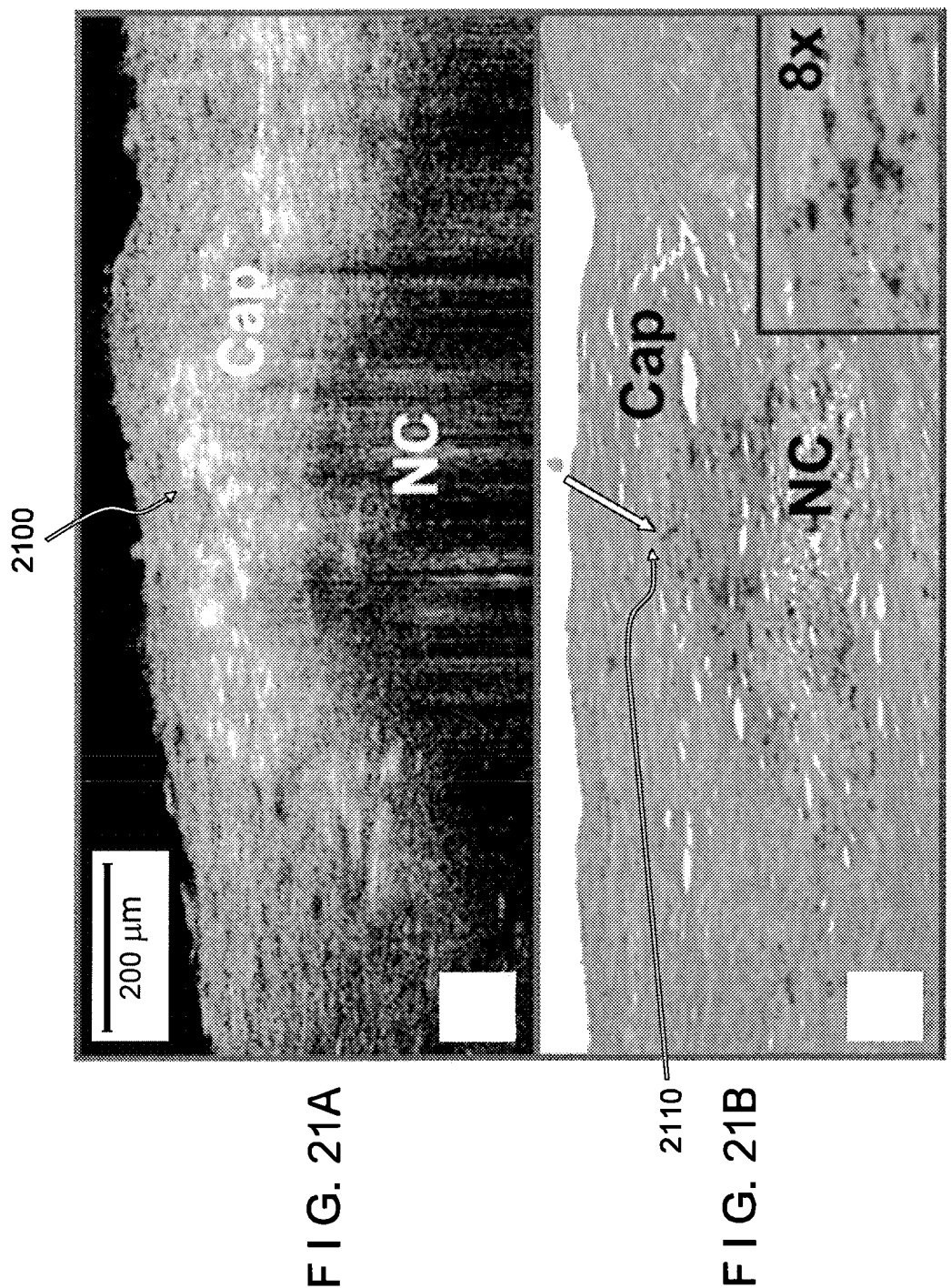
FIG. 21A is an exemplary μOCT image of microcalcifications which can be seen as bright densities within the μOCT image of the fibrous cap.
FIG. 21B is an exemplary μOCT image of the microcalcifications which can be seen as dark densities on the corresponding histology.

FIGS. 20A-20D show further exemplary images which have been generated using the exemplary embodiment(s) of the methods, systems and apparatus according to the present disclosure. FIG. 21A shows an exemplary µOCT image of microcalcifications which are seen as bright densities within the µOCT image of the fibrous cap 2100. FIG. 21B illustrates an exemplary µOCT image of microcalcifications which are seen as purple densities on the corresponding histology 2110.

Further, FIGS. 20A-20D illustrate further exemplary images which have been generated using the exemplary embodiment(s) of the methods, systems and apparatus according to the present disclosure. For example, FIG. 22A shows an exemplary µOCT image of a large calcium nodule, demonstrating disrupted intima/endothelium 2200. FIG. 22B shows an expanded view of an exemplary region enclosed by the red box shows microscopic tissue strands, consistent with fibrin 2210, adjoining the unprotected calcium 2220 to the opposing detached intima. FIG. 22C shows a corresponding histology illustrating fibrin 2230 and denuded calcific surface 2240.

Figures 23A, 23B:
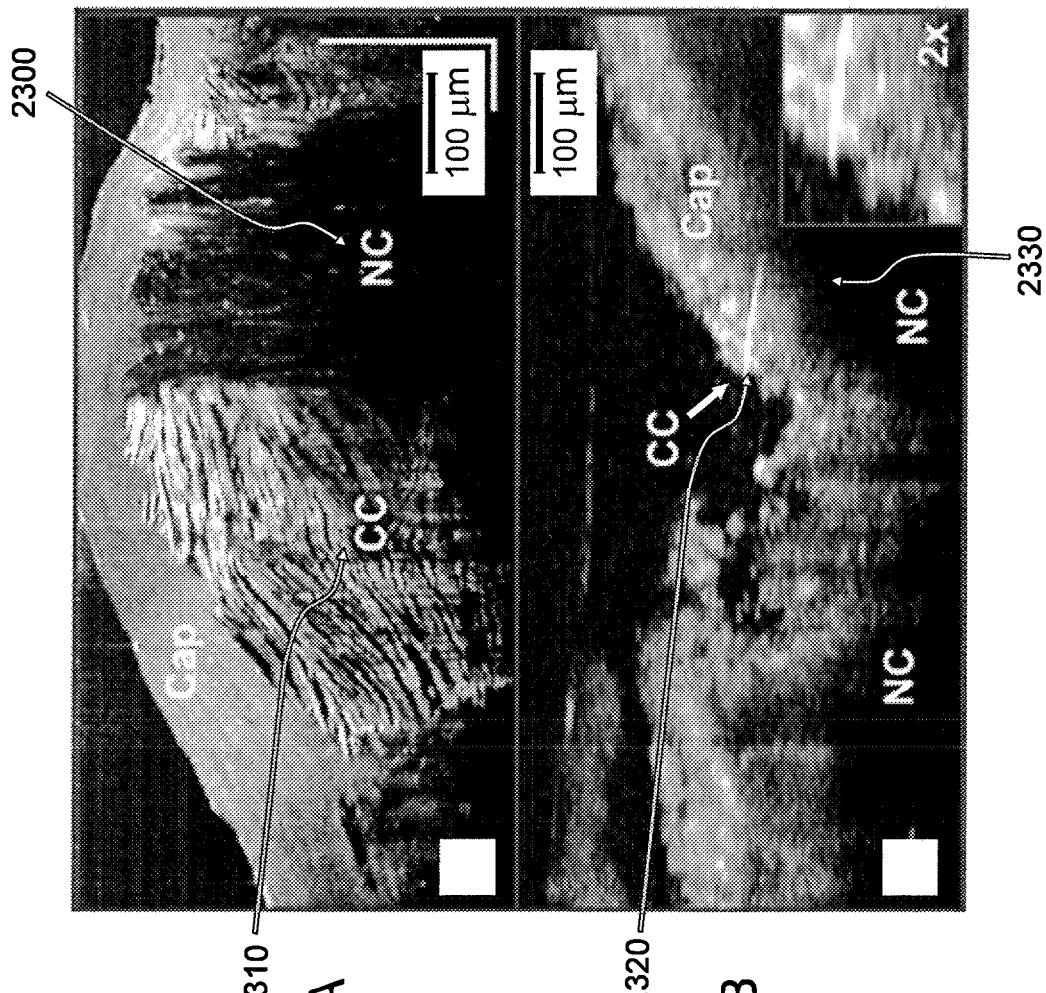
FIG. 23A is an exemplary μOCT image of a large necrotic core (NC) fibroatheroma, demonstrating thick cholesterol crystals (CC), characterized by reflections from their top and bottom surfaces.
FIG. 23B is an exemplary μOCT image of thin crystal (CC, gray arrow) piercing the cap of another necrotic core plaque (NC), shown in more detail in the inset.
Figures 24A, 24B:
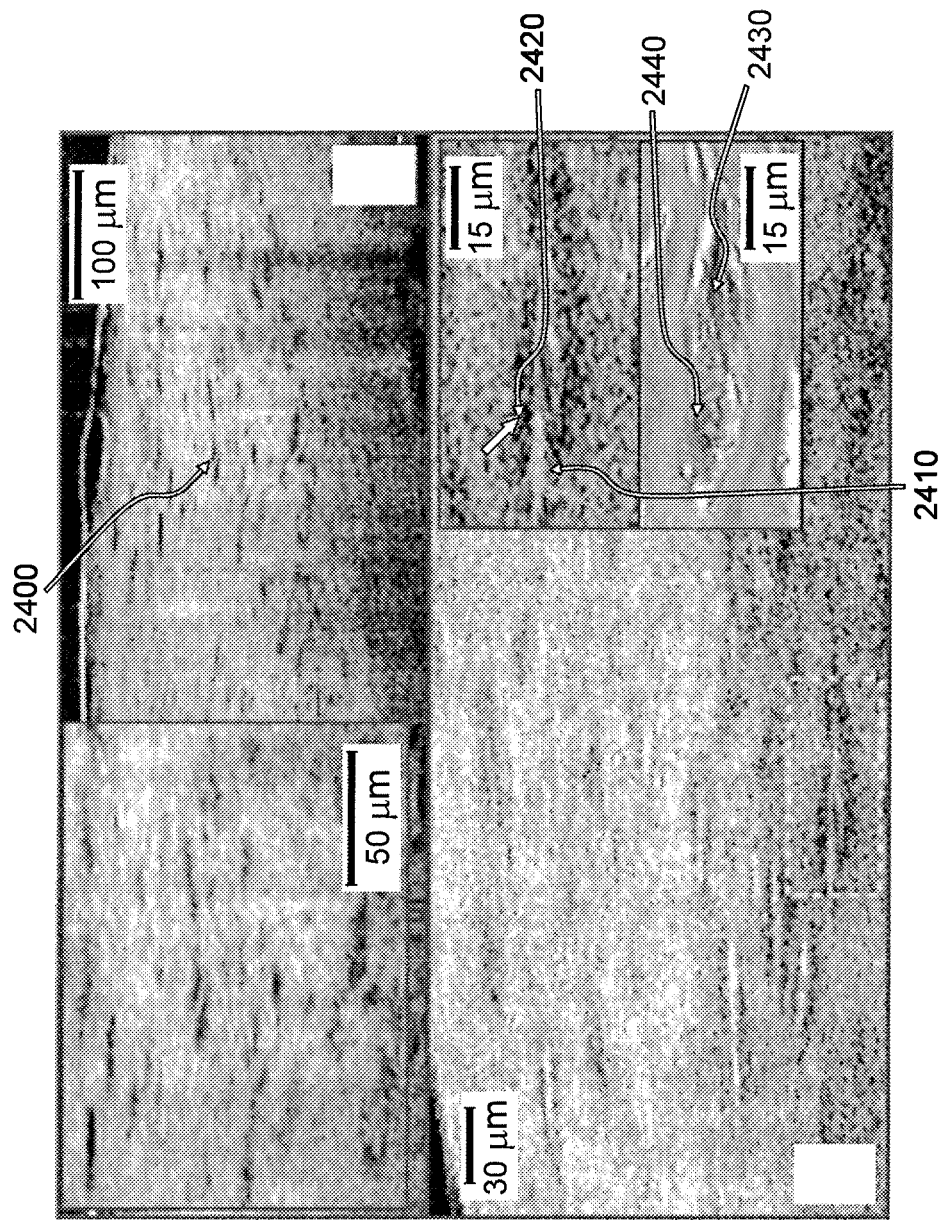
FIG. 24A is an exemplary μOCT image of various smooth muscle cells appearing as low backscattering spindle-shaped cells (inset)
FIG. 24B is an exemplary μOCT image of smooth muscle cells producing collagen are spindle shaped, have a high backscattering interior (light gray arrow) and a "halo" of low backscattering (white arrow), which represents the cell body and collagen matrix, respectively (histology inset)

In addition, FIGS. 23A-26C illustrate further exemplary images which have been generated using the exemplary embodiment(s) of the methods, systems and apparatus according to the present disclosure. For example, FIG. 23A shows an exemplary µOCT image of a large necrotic core 2300 fibroatheroma, demonstrating thick cholesterol crystals 2310, characterized by reflections from their top and bottom surfaces. FIG. 23B shows an exemplary µOCT image of thin crystal 2320, piercing the cap of another necrotic core plaque 2330, shown in more detail in the inset. FIG. 24A shows an exemplary µOCT image of many smooth muscle cells 2400 appear as low backscattering spindle-shaped cells (inset). FIG. 24B shows an exemplary µOCT image of smooth muscle cells producing collagen are spindle shaped, have a high backscattering interior 2410 and a "halo" of low backscattering 2420, which can represent the cell body 2430 and collagen matrix 2440, respectively (e.g., histology inset).

Figures 25A, 25B, 25C:
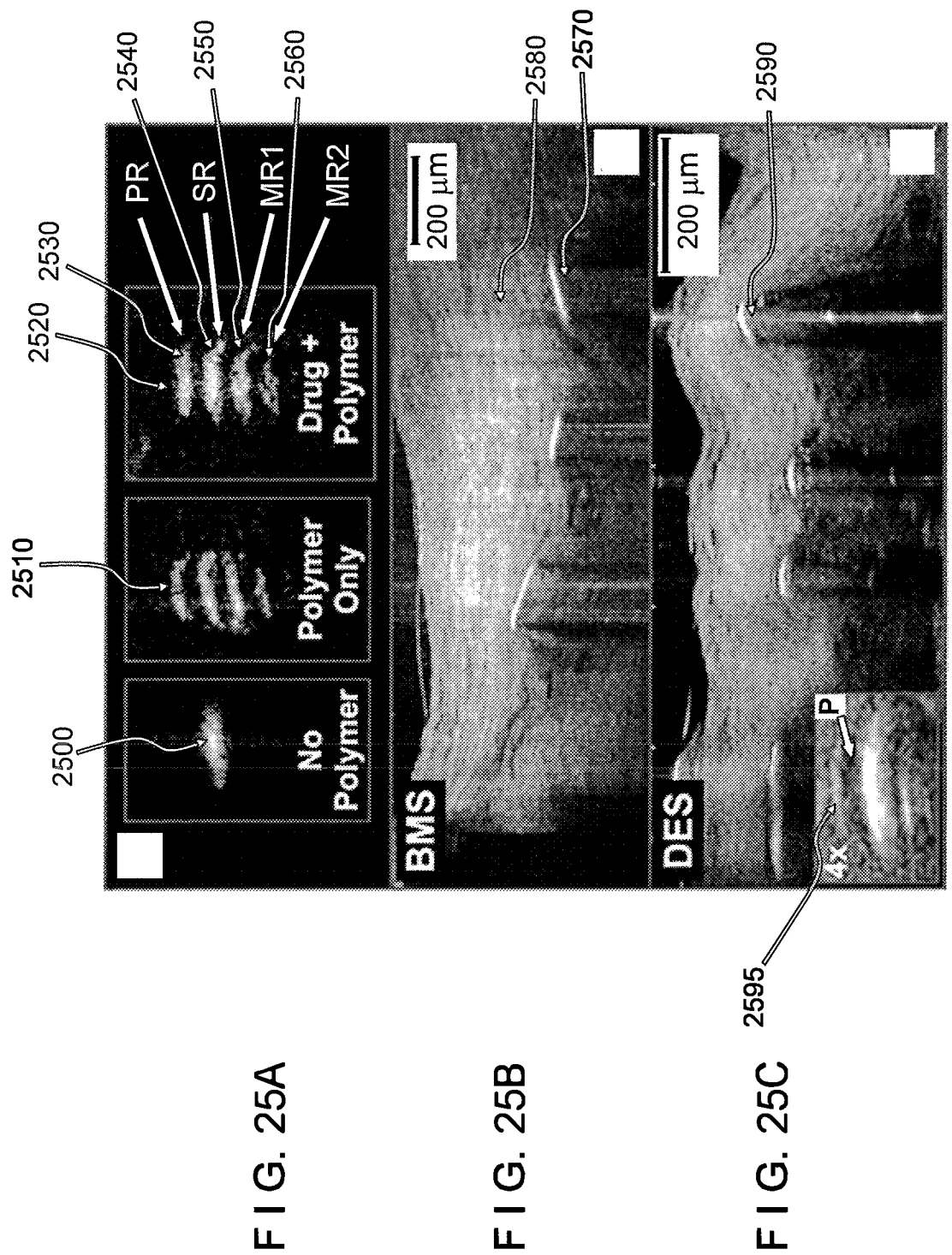
FIG. 25A is an exemplary μOCT image of Taxus Liberte struts with/without polymer/drug, i.e., for polymer-coated struts, polymer reflection (PR), strut reflection (SR) and multiple reflections (MR1, MR2) can be seen.
FIG. 25B is an exemplary μOCT image of a cadaver coronary specimen with an implanted BMS shows struts devoid of polymer, covered by neointima.
FIG. 25C is an exemplary μOCT image of a cadaver coronary specimen with implanted DES struts from another cadaver showing polymer overlying the strut reflections (P, inset)

FIG. 25A shows an exemplary µOCT image of Taxus Liberte (Boston Scientific, Natick, Mass.) struts without polymer 2500, with polymer without drug 2510, and with polymer with drug 2520. For polymer-coated struts, polymer reflection 2530, strut reflection 2540 and multiple reflections 2550 and 2560 can be seen. FIG. 25B shows an exemplary µOCT image of a cadaver coronary specimen with an implanted BMS 2570 shows struts devoid of polymer, covered by neointima 2580. FIG. 25C shows an exemplary µOCT image of a cadaver coronary specimen with implanted DES struts 2590 from another cadaver showing polymer overlying the strut reflections 2595 (inset).

Figures 26A, 26B, 26C, 26D:
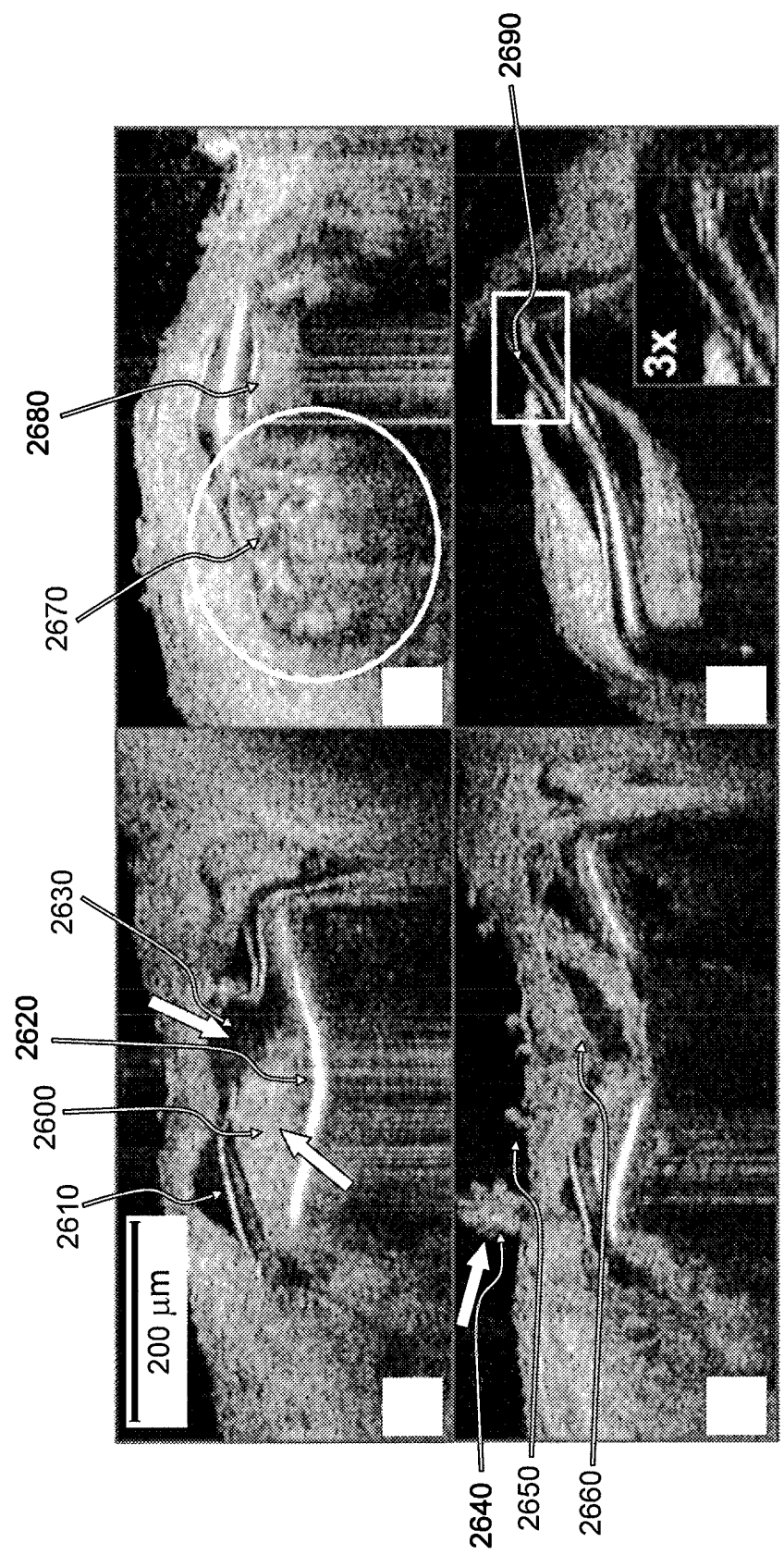
FIG. 26A is an exemplary μOCT image showing tissue (light gray arrow) has separated the polymer off of the stent strut and the polymer has fractured (white arrow)
FIG. 26B is an exemplary μOCT image illustrating a superficial leukocyte cluster (red arrow) and adjacent attached leukocytes overlying the site of the polymer fracture.
FIG. 26C is an exemplary μOCT image illustrating an inflammation at the edge of a strut (dashed region) from another patient.
FIG. 26D is an exemplary μOCT image illustrating an uncovered strut, completely devoid of overlying endothelium (inset)

In addition, FIG. 26A shows an exemplary µOCT image showing tissue 2600 has separated the polymer 2610 off of the stent strut 2620 and the polymer has fractured 2630. FIG. 26B shows an exemplary µOCT image showing superficial leukocyte cluster 2640 and adjacent attached leukocytes 2650 overlying the site of the polymer fracture 2660. FIG. 26C shows an exemplary µOCT image showing inflammation 2670 at the edge of a strut 2680 from another patient. FIG. 26D shows an exemplary µOCT image showing uncovered strut 2690, completely devoid of overlying endothelium.

Figure 27A:
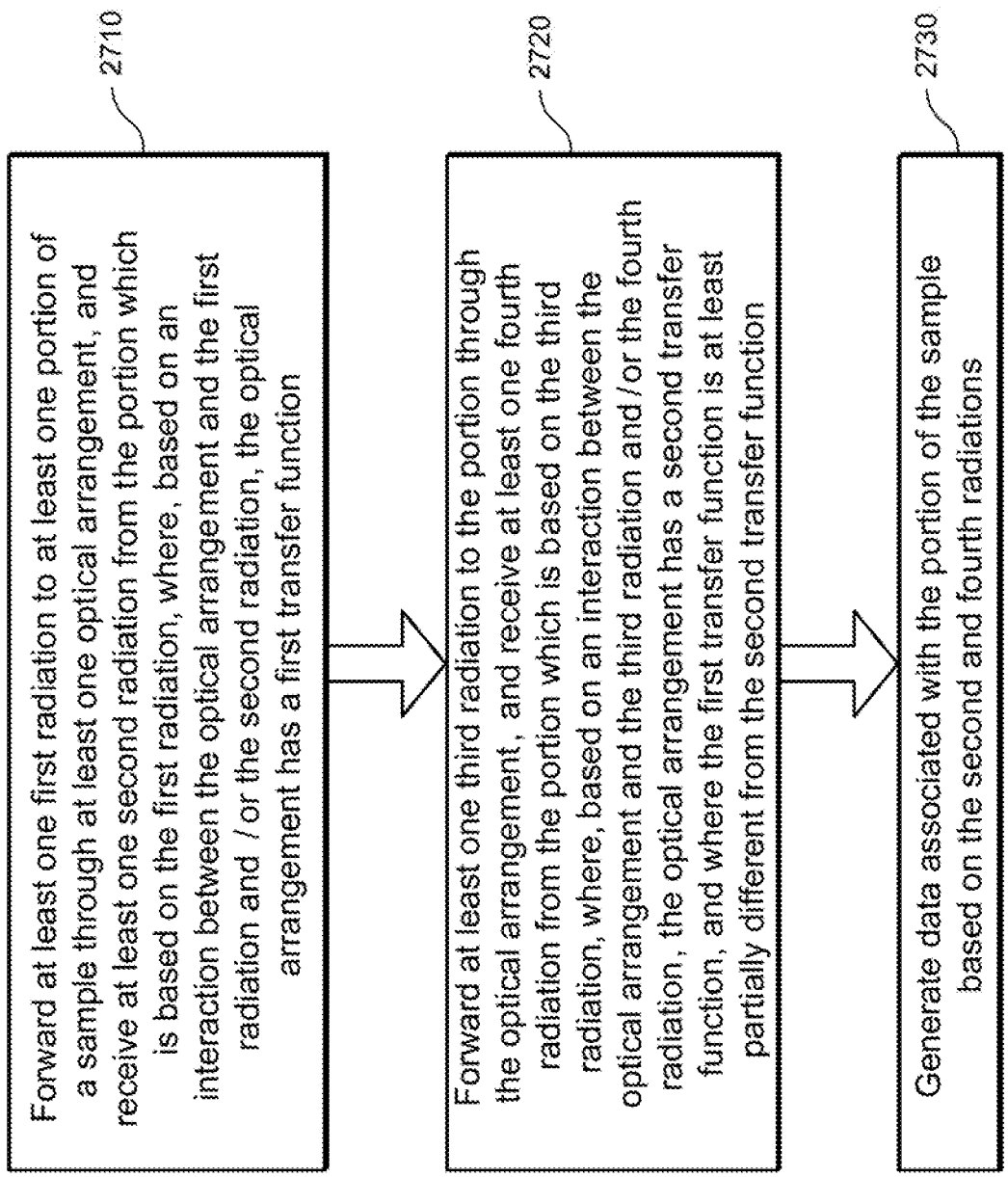
FIG. 27A is a flow diagram of a process according to one exemplary embodiment of the present disclosure.

FIG. 27A shows a flow diagram of a method for providing data associated with at least one portion of at least one sample according to one exemplary embodiment of the present disclosure. For example, in procedure 2710, at least one first radiation is forwarded to at least one portion of the sample through at least one optical arrangement (e.g., as described in various exemplary embodiments herein), and at least one second radiation is received from the portion which is based on the first radiation. Based on an interaction between the optical arrangement and the first radiation and/or the second radiation, the optical arrangement has a first transfer function. Then, in procedure 2720, at least one third radiation is forwarded to the portion through such optical arrangement, and at least one fourth radiation is received from the portion which is based on the third radiation. Based on an interaction between this optical arrangement and the third radiation and/or the fourth radiation, the optical arrangement has a second transfer function. The first transfer function can be at least partially different from the second transfer function. Further, in procedure 2730, the data associated with the portion(s) can be generated based on the second and fourth radiations.

FIG. 27B shows a flow diagram of the method for providing data associated with at least one portion of at least one sample according to another exemplary embodiment of the present disclosure. For example, in procedure 2760, at least one first radiation is forwarded to at least one portion of the sample through at least one first optical arrangement (e.g., as described in various exemplary embodiments herein), and at least one second radiation is received from the portion which is based on the first radiation. Based on an interaction between the first optical arrangement and the first radiation and/or the second radiation, the first optical arrangement has a first transfer function. Then, in procedure 2770, at least one third radiation is forwarded to the portion through at least one second optical arrangement, and at least one fourth radiation is received from the portion which is based on the third radiation. Based on an interaction between the second optical arrangement and the third radiation and/or the fourth radiation, the optical arrangement has a second transfer function. The first transfer function can be at least partially different from the second transfer function. Further, in procedure 2780, the data associated with the portion(s) can be generated based on the second and fourth radiations.

The foregoing merely illustrates the principles of the present disclosure. Various modifications and alterations to the described embodiments will be apparent to those skilled in the art in view of the teachings herein. For example, more than one of the described exemplary arrangements, radiations and/or systems can be implemented to implement the exemplary embodiments of the present disclosure Indeed, the arrangements, systems and methods according to the exemplary embodiments of the present invention can be used with and/or implement any OCT system, OFDI system, SD-OCT system or other imaging systems, and for example with those described in International Patent Application PCT/US2004/029148 filed Sep. 8, 2004 (which published as International Patent Publication No. WO 2005/047813 on May 26, 2005), U.S. patent application Ser. No. 11/266,779 filed Nov. 2, 2005 (which published as U.S. Patent Publication No. 2006/0093276 on May 4, 2006), U.S. patent application Ser. No. 10/861,179 filed Jun. 4, 2004, U.S. patent application Ser. No. 10/501,276 filed Jul. 9, 2004 (which published as U.S. Patent Publication No. 2005/0018201 on Jan. 27, 2005), U.S. patent application Ser. No. 11/445,990 filed Jun. 1, 2006, International Patent Application PCT/US2007/066017 filed Apr. 5, 2007, and U.S. patent application Ser. No. 11/502,330 filed Aug. 9, 2006, the disclosures of which are incorporated by reference herein in their entireties. It will thus be appreciated that those skilled in the art will be able to devise numerous systems, arrangements and methods which, although not explicitly shown or described herein, embody the principles of the present disclosure and are thus within the spirit and scope of the present disclosure. In addition, to the extent that the prior art knowledge has not been explicitly incorporated by reference herein above, it is explicitly being incorporated herein in its entirety. All publications referenced herein above are incorporated herein by reference in their entireties.

What is claimed is:

1. An apparatus for providing illumination of at least one sample, comprising:
    a first wave-guide comprising an optical fiber substantially coaxially aligned with a second, cylindrical wave-guide, the second wave-guide comprising an extended at least partially internally reflecting surface and being configured to (i) transform radiation from the first wave-guide into a plurality of electro-magnetic radiations or a plurality of beams of different orders, and (ii) forward each of the plurality of electro-magnetic radiations or each of the plurality of beams of different orders to at least one lens,
    the optical fiber of the first wave-guide being configured to emit the radiation as a point source directly into the cylindrical second wave-guide; and
    the at least one lens configured to receive the plurality of electro-magnetic radiations or the plurality of beams of different orders from the first wave-guide and the second wave-guide and generate a focus-spot radiation which has a greater depth-of-focus than a depth-of-focus from a single focused beam through the at least one lens.

2. The apparatus of claim 1, wherein the at least one lens is configured to cause the focus-spot radiation to have a diameter that is smaller than a diffraction limited spot on or in the sample.

3. The apparatus of claim 1, wherein the at least one lens includes a GRIN lens.

4. The apparatus of claim 1, wherein the optical fiber of the first wave-guide further comprises a single-mode wave-guide.

5. The apparatus of claim 1, further comprising a housing which at least partially encloses at least one of the first wave-guide or the second wave-guide.

6. The apparatus of claim 5, further comprising a sheath enclosing the housing.

7. The apparatus of claim 5, further comprising a controller which is configured to at least one of rotate or translate the housing.

8. The apparatus of claim 1, wherein the at least one lens includes at least one optical element which comprises a photopolymer.

9. The apparatus of claim 1, wherein the at least one lens comprises two lenses.

10. The apparatus of claim 1, further comprising a swept source,
    wherein the radiation from the first wave-guide is generated by the swept source.

11. The apparatus of claim 1, further comprising a broadband source,
    wherein the radiation from the first wave-guide is generated by the broadband source.

12. The apparatus of claim 1, further comprising an interferometric arrangement provided in communication with the probe.

13. The apparatus of claim 1, wherein the second wave-guide is a multi-mode wave-guide.

14. A probe for providing illumination of at least one sample, comprising:
    a first wave-guide comprising an optical fiber substantially coaxially aligned with a second, cylindrical wave-guide comprising an extended at least partially internally reflecting surface,
    radiation being emitted from an end of the first wave-guide into the second wave-guide to (i) transform the radiation from the first wave-guide into a plurality of electro-magnetic radiations or a plurality of beams of different orders, and (ii) forward each of the plurality of electro-magnetic radiations or each of the plurality of beams of different orders to at least two lenses, and
    the radiation being emitted as a point source from the end of the optical fiber of the first wave-guide directly into the cylindrical second wave-guide; and
    the at least two lenses configured to receive the plurality of electro-magnetic radiations or the plurality of beams of different orders from the first wave-guide and the second wave-guide and generate a focus-spot radiation which has a greater depth-of-focus than a diffraction-limited depth-of-focus.

15. The probe of claim 14, wherein the second wave-guide is a multi-mode wave-guide.

16. A system for imaging at least one sample, comprising:
    a probe comprising a first wave-guide comprising an optical fiber substantially coaxially aligned with a second, cylindrical wave-guide,
    the second waveguide comprising an extended at least partially internally reflecting surface and being configured to convert electro-magnetic radiation emanating from the first wave-guide into a plurality of electro-magnetic radiations, the plurality of electro-magnetic radiations being emitted from an end of the second wave-guide forwarded to at least one lens,
    the electro-magnetic radiation being emanated as a point source from the end of the optical fiber of the first wave-guide directly into the cylindrical second wave-guide;
    an interferometric arrangement provided in communication with the probe; and
    the at least one lens configured to receive the plurality of electro-magnetic radiations from the second wave-guide and generate a focus-spot radiation which has a greater depth-of-focus than a depth-of-focus from a single focused beam through the lens.

17. The system of claim 16, wherein the interferometric arrangement is part of the probe.

18. The system of claim 16, wherein the second wave-guide is a multi-mode wave-guide.

19. An apparatus comprising:
    a first wave-guide comprising an optical fiber, a second, cylindrical wave-guide, a first lens, and a second lens optically coupled to one another and aligned along a single optical axis,
    an end of the first wave-guide comprising a spatially coherent source which emits electro-magnetic radiation toward the second wave-guide,
    the second wave-guide receiving the electro-magnetic radiation emitted from the spatially coherent source and emitting the electro-magnetic radiation toward the first lens,
    the end of the optical fiber of the first wave-guide emitting the electro-magnetic radiation as a point source directly into the cylindrical second wave-guide,
    the second wave-guide comprising an extended at least partially internally reflecting surface and being configured to transform the electro-magnetic radiation to a plurality of beams of different orders, the first lens receiving the electro-magnetic radiation emitted from the second wave-guide and emitting the electromagnetic radiation toward the second lens, and the second lens receiving the electro-magnetic radiation emitted from the first lens and generating a focus-spot radiation which has a greater depth-of-focus than a depth-of-focus from a single focused beam through the first lens.

20. The apparatus of claim 19, wherein the second wave-guide is a multi-mode wave-guide.

21. An apparatus for providing a plurality of electro-magnetic radiations to at least one sample, comprising:

a first wave-guide comprising an optical fiber coaxially aligned with a second, cylindrical wave-guide, the second wave-guide comprising an extended at least partially internally reflecting surface and being configured to (i) transform the plurality of electro-magnetic radiations output from the first wave-guide to a plurality of electromagnetic radiations or a plurality of beams of different orders, and (ii) forward each of the plurality of electro-magnetic radiations or the plurality of beams of different orders to at least two lenses, the optical fiber of the first wave-guide outputting the plurality of electro-magnetic radiations as a point source directly into the cylindrical second wave-guide; and the at least two lenses configured to receive the plurality of electro-magnetic radiations or the plurality of beams of different orders from the first wave-guide and the second wave-guide and generate a focus-spot radiation which has a greater depth-of-focus than a diffraction-limited depth-of-focus.

22. The apparatus of claim 21, wherein the second wave-guide is a multi-mode wave-guide.

* * * * *

UNITED STATES PATENT AND TRADEMARK OFFICE
CERTIFICATE OF CORRECTION

| | |
|---|---|
| PATENT NO. | : 11,633,104 B2 |
| APPLICATION NO. | : 16/577435 |
| DATED | : April 25, 2023 |
| INVENTOR(S) | : Guillermo J. Tearney et al. |

It is certified that error appears in the above-identified patent and that said Letters Patent is hereby corrected as shown below:

In the Specification

Column 13, Line 6, "(n phase" should be --($\pi$ phase--.

Signed and Sealed this
Thirtieth Day of May, 2023

Katherine Kelly Vidal
*Director of the United States Patent and Trademark Office*